US008449918B2

(12) United States Patent
Lapidot et al.

(10) Patent No.: US 8,449,918 B2
(45) Date of Patent: *May 28, 2013

(54) COMPOSITION EXHIBITING ENHANCED FORMULATION STABILITY AND DELIVERY OF TOPICAL ACTIVE INGREDIENTS

(75) Inventors: Noa Lapidot, Mevasseret Zion (IL); Shlomo Magdassi, Jerusalem (IL); David Avnir, Jerusalem (IL); Claudi Rottman, Jerusalem (IL); Orit Gans, Efralm (IL); Alon Seri-Levy, Rehovot (IL)

(73) Assignee: Sol-Gel Technologies Ltd., Beit Shemesh (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/243,189

(22) Filed: Sep. 23, 2011

(65) Prior Publication Data

US 2012/0015014 A1    Jan. 19, 2012

Related U.S. Application Data

(63) Continuation of application No. 12/818,924, filed on Jun. 18, 2010, now Pat. No. 8,039,020, which is a continuation of application No. 09/983,229, filed on Oct. 23, 2001, now Pat. No. 7,758,888, which is a continuation-in-part of application No. PCT/IL01/00370, filed on Apr. 20, 2001.

(60) Provisional application No. 60/198,749, filed on Apr. 21, 2000.

(51) Int. Cl.
*A61K 9/14* (2006.01)
*A61K 9/00* (2006.01)
*A61K 31/07* (2006.01)
*A61K 31/19* (2006.01)
*A61K 31/327* (2006.01)

(52) U.S. Cl.
USPC ............ 424/489; 514/557; 514/714; 514/725

(58) Field of Classification Search
USPC ........................... 424/489; 514/557, 714, 725
See application file for complete search history.

(56) References Cited

U.S. PATENT DOCUMENTS

| 2,885,366 | A | 5/1959 | Iler |
| 3,785,798 | A | 1/1974 | Horai et al. |
| 3,826,670 | A | 7/1974 | Rees et al. |
| 3,957,971 | A | 5/1976 | Oleniacz |
| 4,129,645 | A | 12/1978 | Barnett et al. |
| 4,169,069 | A | 9/1979 | Unger et al. |
| 4,349,456 | A | 9/1982 | Sowman |
| 4,350,681 | A | 9/1982 | Fulton, Jr. |
| 4,361,584 | A | 11/1982 | Fulton, Jr. |
| 4,387,107 | A | 6/1983 | Klein et al. |
| 4,444,746 | A | 4/1984 | Harvey et al. |
| 4,464,317 | A | 8/1984 | Thies et al. |
| 4,497,794 | A | 2/1985 | Klein et al. |
| 4,606,913 | A | 8/1986 | Aronson et al. |
| 4,671,956 | A | 6/1987 | Bouillon et al. |
| 4,686,211 | A | 8/1987 | Hara et al. |
| 4,690,825 | A | 9/1987 | Won |
| 4,692,329 | A | 9/1987 | Klein et al. |
| 4,891,211 | A | 1/1990 | Winston |
| 4,931,362 | A | 6/1990 | Zsifkovits et al. |
| 4,960,772 | A | 10/1990 | Sebag et al. |
| 4,988,744 | A | 1/1991 | Yamamoto |
| 5,086,075 | A | 2/1992 | DeVillez |
| 5,126,915 | A | 6/1992 | Pepin et al. |
| 5,145,675 | A | 9/1992 | Won |
| 5,165,914 | A | 11/1992 | Vlock |
| 5,200,334 | A | 4/1993 | Dunn et al. |
| 5,223,250 | A | 6/1993 | Mitchell et al. |
| 5,292,801 | A | 3/1994 | Avnir et al. |
| 5,387,622 | A | 2/1995 | Yamamoto |
| 5,446,028 | A | 8/1995 | Klein et al. |
| 5,455,048 | A | 10/1995 | Lahmani et al. |
| 5,466,446 | A | 11/1995 | Stiefel et al. |
| 5,500,223 | A | 3/1996 | Behan et al. |

(Continued)

FOREIGN PATENT DOCUMENTS

AU      764016 B2      5/2002
DE      19811900 A1    9/1999

(Continued)

OTHER PUBLICATIONS

Office Action issued Jan. 5, 2011, in connection with U.S. Appl. No. 12/818,924.
Response filed to Office Action of Jan. 5, 2011(including amendment, IDS and Terminal Disclaimer) filed Apr. 5, 2011 in U.S. Appl. No. 12/818,924.
Hawley's Condensed Chemical Dictionary, Thirteenth Edition, pp. 480 and 1066 (1997).
Request for Reexamination, filed Jan. 18, 2011 for U.S. Patent No. 7,758,888.
Osseo-Asare, K., Hydrolysis of silicon alkoxides in microemulsions, Surfactan Sci. Sek., 42:147-188 (2000).
Goto, et al, "Controlled dissolution of ohenytoid by hybridizing with silica nanoparticles", Journal of Nanoparticle Research. (1999). 1:205-213.

(Continued)

*Primary Examiner* — James H Alstrum Acevedo
(74) *Attorney, Agent, or Firm* — Browdy and Neimark, PLLC

(57) ABSTRACT

A therapeutic, cosmetic or cosmeceutic composition for topical application, capable of stabilizing an active ingredient and delivering the active ingredient, comprising a plurality of microcapsules having a core-shell structure. The microcapsules have a diameter of approximately 0.1 to 100 micron. The core of each microcapsule includes at least one active ingredient, and is encapsulated within a microcapsular shell. The shell is comprised of at least one inorganic polymer obtained by a sol-gel process, and the shell protects the active ingredient before topical application and is designed to release the active ingredient from the microcapsules following application. The composition is useful in encapsulating active ingredients, such as benzoyl peroxide, that are unstable in other formulation, or are irritating to the skin.

14 Claims, 5 Drawing Sheets

U.S. PATENT DOCUMENTS

| | | | |
|---|---|---|---|
| 5,520,917 A | 5/1996 | Mizuguchi et al. |
| 5,556,617 A | 9/1996 | Ribier et al. |
| 5,587,170 A | 12/1996 | Caisey et al. |
| 5,591,453 A | 1/1997 | Ducheyene et al. |
| 5,607,664 A | 3/1997 | Ascione et al. |
| 5,632,996 A | 5/1997 | Ramirez et al. |
| 5,635,809 A | 6/1997 | Levy et al. |
| 5,650,311 A | 7/1997 | Avnir et al. |
| 5,670,209 A | 9/1997 | Wyckoff |
| 5,672,301 A | 9/1997 | Orly et al. |
| 5,691,060 A | 11/1997 | Levy |
| 5,700,451 A | 12/1997 | Yue et al. |
| 5,733,531 A | 3/1998 | Mitchnick et al. |
| 5,739,020 A | 4/1998 | Pope |
| 5,767,098 A | 6/1998 | Klein et al. |
| 5,785,977 A | 7/1998 | Breithbarth |
| 5,851,538 A | 12/1998 | Froix et al. |
| 5,874,105 A | 2/1999 | Watkins et al. |
| 5,876,699 A | 3/1999 | DiSomma et al. |
| 5,879,716 A | 3/1999 | Katz et al. |
| 5,895,757 A | 4/1999 | Pope |
| 5,906,811 A | 5/1999 | Hersh |
| 5,912,016 A | 6/1999 | Perrier et al. |
| 5,914,101 A | 6/1999 | Tapley et al. |
| 5,932,228 A | 8/1999 | Hall et al. |
| 5,955,109 A | 9/1999 | Won et al. |
| 5,962,517 A | 10/1999 | Murad |
| 5,998,392 A | 12/1999 | Simard et al. |
| 6,013,637 A | 1/2000 | Klein et al. |
| 6,015,548 A | 1/2000 | Siddiqui et al. |
| 6,074,629 A | 6/2000 | Kostinko |
| 6,077,522 A | 6/2000 | Scher et al. |
| 6,090,399 A | 7/2000 | Ghosh et al. |
| 6,103,267 A | 8/2000 | Mitchnick et al. |
| 6,117,843 A | 9/2000 | Baroody et al. |
| 6,132,773 A | 10/2000 | Amiche |
| 6,143,280 A | 11/2000 | Pike et al. |
| 6,146,664 A | 11/2000 | Siddiqui |
| 6,171,600 B1 | 1/2001 | Dahms |
| 6,197,757 B1 | 3/2001 | Perrier et al. |
| 6,217,852 B1 | 4/2001 | Gildenberg et al. |
| 6,238,650 B1 | 5/2001 | Lapidot et al. |
| 6,242,099 B1 | 6/2001 | Grandmontagne et al. |
| 6,251,313 B1 | 6/2001 | Deubzer et al. |
| 6,280,746 B1 | 8/2001 | Arquette et al. |
| 6,303,149 B1 | 10/2001 | Magdassi et al. |
| 6,337,089 B1 | 1/2002 | Yoshioka et al. |
| 6,436,375 B1 | 8/2002 | Lapidot et al. |
| 6,468,509 B2 | 10/2002 | Lapidot et al. |
| 6,495,352 B1 | 12/2002 | Brinker et al. |
| 6,537,583 B1 | 3/2003 | Dupuis et al. |
| 6,607,713 B1 | 8/2003 | Chodorowski et al. |
| 6,616,947 B1 | 9/2003 | Depuis |
| 6,646,947 B2 | 11/2003 | Fukui et al. |
| 6,703,032 B2 | 3/2004 | Gers-Barlag et al. |
| 6,855,335 B2 | 2/2005 | Seok et al. |
| 7,758,888 B2 * | 7/2010 | Lapidot et al. ............ 424/489 |
| 8,039,020 B2 * | 10/2011 | Lapidot et al. ............ 424/489 |
| 2002/0151527 A1 | 10/2002 | Wiegand et al. |
| 2003/0170196 A1 | 9/2003 | Orsoni et al. |
| 2005/0208134 A1 | 9/2005 | Magdassi et al. |
| 2006/0251687 A1 | 11/2006 | Lapidot et al. |
| 2007/0003585 A1 | 1/2007 | Clark et al. |

FOREIGN PATENT DOCUMENTS

| | | |
|---|---|---|
| EP | 0281034 | 9/1988 |
| EP | 0462388 A2 | 12/1991 |
| EP | 0581651 | 2/1994 |
| EP | 0581651 A2 | 2/1994 |
| EP | 0680753 A2 | 11/1995 |
| EP | 0934773 | 8/1999 |
| EP | 0934773 A2 | 8/1999 |
| EP | 0972563 A1 | 1/2000 |
| FR | 2703927 A1 | 10/1994 |
| FR | 2774906 A1 | 8/1999 |
| FR | 2780901 A1 | 1/2000 |
| GB | 1399344 | 7/1975 |
| GB | 2416524 A | 2/2006 |
| JP | 02-002867 A2 | 1/1990 |
| JP | 2040302 | 2/1990 |
| JP | 02-251240 A2 | 10/1990 |
| JP | 03229634 | 10/1991 |
| JP | 07173452 A2 | 7/1995 |
| JP | 09110463 A2 | 4/1997 |
| JP | 09-235217 A2 | 9/1997 |
| JP | 01-113436 A2 | 2/1998 |
| WO | 9404260 A1 | 3/1994 |
| WO | 9404261 A1 | 3/1994 |
| WO | 97/32561 A1 | 9/1997 |
| WO | 9740106 | 10/1997 |
| WO | 9745367 A1 | 12/1997 |
| WO | 98/15183 A1 | 4/1998 |
| WO | 9831333 | 7/1998 |
| WO | 9903450 A1 | 1/1999 |
| WO | 0009652 | 2/2000 |
| WO | 0025761 | 5/2000 |
| WO | 0025761 A1 | 5/2000 |
| WO | 0025908 A1 | 5/2000 |
| WO | 0072806 | 7/2000 |
| WO | 0047236 | 8/2000 |
| WO | 0071084 | 11/2000 |
| WO | 0112221 A1 | 2/2001 |
| WO | 0113924 A1 | 3/2001 |
| WO | 02/085113 A1 | 10/2002 |
| WO | 03039510 A1 | 5/2003 |
| WO | 03/066209 A1 | 8/2003 |
| WO | 2004/069216 A1 | 8/2004 |
| WO | 2004/081222 A2 | 9/2004 |
| WO | 2005/009604 A1 | 2/2005 |
| WO | 2007/000316 A1 | 1/2007 |
| WO | 2007036939 A3 | 2/2007 |
| WO | 2007015243 A3 | 4/2007 |

OTHER PUBLICATIONS

Valet-Regi, et al, "A new property of MCM-41: Drug delivery system". Chem. Mater. (2001). 13: 308-311.

Aizawa, et al., "Preparation of Spherical Hydrous Silica Oxide Particles under Acidic Condition via Sol-Gel Processing", Journal of Sol-Gel Science and Technology, (2000), 19:329-332.

Barbé, et al., "Sol-gel Microspheres and Nanospheres for Controlled Release Applications", Controlled Release Society 29th Annual Meeting Proceedings, (2002), p. 545-546.

Butler, et al., "An Emulsion Method for Producing Fine, Low Density, High Surface Area Silica Powder from Alkoxides", Journal of Material Science, (1996), 31:1675-1680.

Nakatsuka, et al., "Surface Modification of Inorganic Pigments with Organic UV Absorbers", Colloid Surface, (1988/89), 34:323-334.

Tatapudy, et al., "Benzoyl Peroxide Microcapsules I. Preparation of Core Material", Indian Drugs, (1995), 32 (6):239-248.

Hench, Larry L. et al., "The Sol-Gel Process", Chem. Rev. 1990, vol. 90, pp. 33-72.

Merriam Webster's Collegiate Dictionary, 10th edn., Merriam-Webster, Inc: Springfield, Massachusetts, 1996, pp. 717 and 1079.

Midmore, B. R., "Preparation of a Novel Silica-Stabilized Oil/Water Emulsion", Colloids and Surfaces A: Physicochemical and Engineering Aspects, vol. 132, pp. 257-265 (1998).

Duyan Dai, A study on the Technique of Preparing Microcapsules Via In Situ Polymerization and the Application Thereof, Journal of Tianjin Institute of Textile Science and Technology, 1994, 13 (1), 95-101 English Translation.

Avnir et al., "Organic Fluorescent Dyes Trapped in Silica and Silica-Titania Films by the Sol-Gel Method Photophysical, Film and Cage Properties," Journal of Non-Crystalline Solids 74, (1985), 395-406.

Kumar, M.N.V. Ravi, "Nano and Microparticles as Controlled Drug Delivery Devices", J. Pharm. Pharmaceutic. Sci. 3(2)234-258, (2000).

Sol-Gel Science, The Physics and Chemistry of Sol-Gel Processing, C. Jeffrey Brinker, George W. Scherer, May 1990, (pp. 562-563).

Iqball Gill et al. "Encapsulation of Biologicals within Silicate, Siloxane, and Hybrid Sol-Gel Polymers: An Efficient and Generic Approach", J. Am. Chem. Soc. vol. 120, pp. 8587-8598, (1998).

Hou et al..; "Improvement of photofatigue resistance of spirooxazine entrapped in organic-inorganic composite synthesized via the sol-gel method," SPIE, vol. 2288 Sol-Gel Optics III, (1994), 328-339.

Bugnon, P., "Surface treatment of pigments. Treatment with inorganic materials", Progress in Organic Coatings, vol. 29, pp. 39-43, (1996).

Hall, S., et al., "Cocondensation of Organosilica Hybrid Shells on Nanoparticle, Templates: A Direct Synthetic Route to Functionalized Core—Shell Colloids", Langmuir, vol. 16, pp. 1454-1456, (2000).

Haq et al., "Preparation and properties of uniform coated inorganic colloidal particles 9. Titania on copper compounds", Colloids and Surfaces A: Physicochemical and Engineering Aspects, vol. 81, pp. 153-159, (1993).

Hsu et al, "Paper Whiteners I. Titania Coated Silica", Journal of Colloid and Interface Science, vol. 156, pp. 56-65, (1993).

Iler, R., "Silica Gels", The Chemistry of Silica, pp. 510-533, (1979).

Lapidot, et al., "Advanced Sunscreens: UV Absorbers Encapsulated in Sol-Gel Glass Microcapsules", Journal of Sol-Gel Science and Technology, pp. 67-72, vol. 26, (2003).

Magdassi, S. et al., Cosmceutic and Delivery Systems in Novel Cosmetics Delviery System, S. Magdassi, E. Touitou Eds., Dekker Inc., (1999).

Matijevi et al, "Note: Coating of Nanosize Silver Particles with Silica", Journal of Colloid and Interface Science, pp. 133-136, vol. 221, (2000).

Mikrajuddin, et al., "Stable photoluminescence of zinc oxide quantum dots in silica nanoparticles matrix prepared by the combined sol-gel and spray drying method", Journal of Applied Physics, pp. 6431-6434, vol. 89, No. 11, (2001).

Rottman, C., et al, "Advanced Sunscreens: UV Absorbers Entrapped in Glass Microcapsules", Euro Cosmetics, pp. 20-22, (2000).

Rottman, C., et al. "Sol-Gel Products News: Advanced Sunscreens: UV Absorbers Entrapped in Sol-Gel Glass Microcapsules", Journal of Sol-Gel Science and Technology, pp. 268-270, vol. 23, (2002).

Van Bruggen, et al., "Preparation and Properties of Colloidal Core-Shell Rods with Adjustable Aspect Ratios", Langmuir, pp. 2245-2255, vol. 14, No. 9, (1998).

* cited by examiner

US 8,449,918 B2

COMPOSITION EXHIBITING ENHANCED FORMULATION STABILITY AND DELIVERY OF TOPICAL ACTIVE INGREDIENTS

FIELD OF THE INVENTION

The present invention relates to a composition for topical application, which comprises therapeutic, cosmetic or cosmeceutic active ingredients encapsulated in sol-gel microcapsules and which is designed to stabilize and deliver the encapsulated active ingredients. More particularly, the composition of the present invention is designed to protect ingredients that decompose when in contact with oxygen, water or with other ingredients of the topical formulation, thus enhancing the stability of these sensitive ingredients in the formulation, and is further designed to release the encapsulated ingredients following a topical application, through a pre-designed release mechanism, thus acting as a delivery system.

The present invention further relates to a process for preparing the microcapsules of the present invention; to methods of delivering the active ingredients from the composition of the present invention; and to uses of the composition of the present invention in the treatment of conditions, diseases and disorders such as, but not limited to, acne, psoriasis, infections and inflammatory processes.

BACKGROUND OF THE INVENTION

Many active ingredients which are recognized as beneficial for to improving skin or hair condition and feeling, for reducing signs of aging and photoaging or for the treatment of skin disorders such as acne, psoriasis, seborrhea and infections, are difficult to formulate in cosmetic compositions or in pharmaceutical preparations. Often these active ingredients decompose when in contact with water, oxygen, oxidants, trace amounts of metallic ions, or with components commonly used in cosmetic or dermatological compositions. Consequently, the shelf life of products containing these ingredients is reduced. Another prevalent problem is that while being effective in treating the skin, many of these active ingredients cause skin irritation. A delivery system for sustained release can contribute to decreasing such irritation by reducing the concentration of active ingredients that are in contact with the skin or hair, at any given moment. In addition, sustained release can extend the duration of activity of the ingredient.

Perfumes are an example of an ingredient that is frequently added to pharmaceutical, cosmetic or cosmeceutic compositions. Perfumes, while having no therapeutic action, often cause skin irritation. Entrapment of perfumes may serve to decrease skin sensitivity to perfumes, while extending their period of effectiveness through the mechanism of sustained release. Colors and dyes can also benefit from entrapment, since they are often incompatible with other formulation ingredients.

Various formulations have been developed to address these problems. Improved emulsions of water-in-oil or oil-in-water have been developed, such as that described in U.S. Pat. No. 6,171,600, which discloses use of a double emulsion, U.S. Pat. No. 5,851,538 discloses a protection system based on the adsorption of the active ingredient in pores that are present in an organic polymer in a sponge form, U.S. Pat. No. 3,957,971 and U.S. Pat. No. 5,874,105 utilize liposomes as a delivery system.

U.S. Pat. No. 6,103,267 and U.S. Pat. No. 6,146,664 show that sensitive active ingredients, such as Vitamin A and Vitamin C, can be stabilized as dispersions in a non-solvent and still be active when applied on the skin. A similar approach was used in U.S. Pat. No. 6,077,522, for stabilizing biologically active compounds for various uses.

FR 2780901, WO 99/03450. FR 2703927, WO 94/04260 and WO 94/04261 disclose microparticles and nanoparticles for encapsulation of cosmetics, pharmaceutics and food compositions, which include cell walls that are formed by cross-linking of organic and bio-organic polymers.

All the formulations described hereinabove employ organic or, bio-organic matrices for stabilizing the active ingredients prior to their use. Organic polymers are inherently more susceptible to chemical and photochemical damage as compared with inorganic polymers. In addition, organic and bio-organic matrices are highly sensitive to shear forces, osmotic pressure, heat, etc., and therefore, tend to release substantially the entire content of active ingredients contained therein immediately following to application, hence failing to provide controlled stabilization and delivery.

Another ingredient that is frequently added to pharmaceutical, cosmetic or cosmeceutic compositions, particularly to anti-acne and dental compositions, is benzoyl peroxide. Such compositions often include a combination of benzoyl peroxide, as a dispersion, and other active ingredients, such as retinoids and antibiotics, which typically exert a synergistic effect in the treatment of acne and other skin or dental conditions, diseases and disorders. However, the preparation and use of these compositions is limited since benzoyl peroxide is a highly reactive oxidation agent and therefore oxidizes the additional active ingredients. Therefore, the presently known formulations that include benzoyl peroxide are typically characterized by limited stability and short shelf life, hence, separate containers are often used for each of the active ingredients.

U.S. Pat. No. 6,013,637 discloses an anti-acne composition which includes benzoyl peroxide and lycomycin. The disclosed composition is stable for one month. Indeed, this patent further discloses an end product which includes separate kits for the benzoyl peroxide and the antibiotic agent U.S. Pat. No. 4,350,681 discloses a method of stabilizing benzoyl peroxide in a dispersion and a method of treating acne using a benzoyl peroxide composition and a retinoic acid composition. Indeed, the method disclosed in this patent comprises separate topical application of the compositions at a time interval of 10 minutes.

Hence, the prior art fails to teach a delivery system that provides protection of naive active ingredients from benzoyl peroxide and/or other harsh substances prior to their application. The prior art also fails to disclose a stabilizing system designed to release the active ingredients upon topical application.

Another media for controlled delivery of drugs, which can be utilized to protect sensitive ingredients, is doping within sol-gel matrices. In this method, monoliths, particles or other forms (such as thin layers, or fibers) are prepared, and the active ingredient is immobilized in the pores of the sol-gel matrix. The sol-gel matrix is doped with small amounts of the active ingredient. This method is utilized in U.S. Pat. No. 5,591,453, WO 97/45367, U.S. Pat. No. 4,169,699. DE 19811900. WO 00/47236, U.S. Pat. No. 4,988,744. JP 07173452. WO 01/12221. JP 09110463 WO 01/13924 and EP 281034, and is further disclosed in Goto et al., Nanoparticles Res. 1 (1999), 205 and in Vallet-Regi et al., Chem. Mater. 13 (2001), 308.

However, sol-gel doped matrices cannot support high loading (of up to 95% wt.) of the active ingredient. In order to obtain high loading, it is essential to form a core-shell structure, where most of the weight of the capsule is the weight of the encapsulated active ingredient (core), and where the thin shell protects the core effectively, U.S. patent application Ser. No. 09/372,176 discloses a method for the preparation of silica microcapsules containing organic compounds for various uses. This method was utilized in the development of encapsulated sunscreen active ingredients, disclosed in U.S. Pat. No. 6,238,650; where active ingredients are highly retained within the silica capsules, minimizing exposure of the skin to the active ingredient. Sol-gel microcapsules of silica, when formed according to U.S. patent application Ser. No. 09/372,176, are chemically and photochemically stable, inert and safe for use. When incorporated in cosmetic or pharmaceutical compositions they afford a transparent, cosmetically pleasing product. The hydrophobic/hydrophilic character of the capsules is tailored to suit the purpose, by selecting appropriate sol-gel precursors and reaction conditions. Selection of the makeup of the microcapsule precursors, determines the character of the microcapsular shell surrounding the active ingredient. Thus, for instance, hydrophobicity/hydrophilicity can be controlled, so that water-soluble actives and oil-soluble actives can both be present in the same formulation, by encapsulation of one or the other. It is possible to encapsulate hydrophobic materials, that would have required the presence of large quantities of oils in the formulation, in silica, which has a hydrophilic extetrnal surface, allowing easy incorporation into aqueous phases. Generally, water based products or emulsions such as oil-in-water emulsions with external water phase are considered to afford improved feel on the skin, and are therefore preferred in many cases over oil-based products (ointments) or water-in-oil emulsions. For that reason it is desirable to have a delivery system that is water dispersible, to allow easy incorporation in the water phase.

Thus, U.S. patent application Ser. No. 09/372,176 and U.S. Pat. No. 6,238,650 (both incorporated herein by reference) disclose microcapsule formulations specifically designed to prevent an encapsulated active ingredient from leaving the microcapsule. This is desirable when the active ingredient is an irritant to the body tissue to which it is applied. It is also desired when the active ingredient acts by interaction with light, such as sunlight. However, U.S. patent application Ser. No. 09/372,176 and U.S. Pat. No. 6,238,650 fail to disclose compositions and methods for releasing and hence delivering the active ingredients.

Thus, a system that is capable of both holding and protecting the sensitive active ingredient in the formulation and of releasing and hence delivering the active ingredient upon application is not disclosed by the prior art. Such a system can serve to shield and protect active ingredients from undesired decomposition, thus extending the shelf life of the composition and may also serve to segregate incompatible agents present in the same composition during storage. Furthermore, the activity of the active ingredients can be optimized as a result of sustained release, while skin irritation can be reduced, since there is a significant reduction in the concentration of active ingredient in direct contact with the skin, at any given time.

There is thus a widely recognized need for, and it would be highly advantageous to have compositions for topical application that include therapeutic, cosmetic or cosmeceutic active ingredients encapsulated in sol-gel microcapsules, which are designed to stabilize and deliver the active ingredients encapsulated therein.

SUMMARY OF THE INVENTION

While evaluating the potential use of sol-gel microcapsules it was surprisingly discovered that sol-gel microcapsules could be designed to achieve triggered release of their content upon application in a sustained or an immediate manner. It was discovered that compositions comprising pre-designed sol-gel microcapsules are capable of protecting sensitive and/or incompatible active ingredients, such as an antibiotics and benzoyl peroxide, prior to topical application, and are thus characterized by increased stability and extended shelf life. It was further discovered that these compositions could be designed to release the active ingredients following topical application, and therefore function as a delivery system of the encapsulated ingredients.

Hence, according to one aspect of the present invention, there is provided a therapeutic, cosmetic or cosmeceutic composition for topical application comprising a plurality of microcapsules each having a core-shell structure, wherein the core is a microcapsular core encapsulated within the shell and includes on or more active ingredient(s), whereas the shell is a microcapsular shell and includes one or more inorganic polymer(s) obtained by a sol-gel process.

According to further features in preferred embodiments of the invention described below, the composition is designed to stabilize the one or more active ingredient(s) prior to the topical application and/or to release the one or more active ingredient(s) from the microcapsules following the topical application.

According to another aspect of the present invention there is provided a system for enhancing a stability of one or more active ingredient(s) in the therapeutic, cosmetic or cosmeceutic composition for topical application of the present invention, the system comprising a plurality of microcapsules as described hereinabove and is designed to stabilize the one or more active ingredient(s) prior to the topical application.

According to further features in preferred embodiments of the invention described below, the system is designed to release the one or more active ingredient(s) from said microcapsules following the topical application.

According to yet another aspect of the present invention there is provided a system for releasing/delivering one or more active ingredient(s) from the therapeutic, cosmetic or cosmeceutic composition for topical application of the present invention, the system comprising a plurality of microcapsules as described hereinabove and is designed to release the one or more active ingredient(s) from the microcapsules following the topical application.

According to further features in preferred embodiments of the invention described below, the system is designed to stabilize the one or more active ingredient(s) prior to the topical application.

According to still another aspect of the present invention there is provided a method of treating a skin, hair, ear, mucosal membrane, rectal, nasal or dental condition in a subject in need thereof the method comprising topically applying onto a skin, hair, ear, mucosal membrane, rectum, nose or tooth the composition of the present invention.

According to further features in preferred embodiments of the invention described below, the skin, hair, ear, mucosal membrane, rectal, nasal or dental condition comprises a condition, disease or disorder selected from the group consisting of acne, psoriasis, seborrea, bacteria virus, fungus, infection, inflammation, aging signs, dandroofs and cavity.

According to an additional aspect of the present invention there is provided a method of delivering an active ingredient from the therapeutic, cosmetic or cosmeceutic composition for topical application of the present invention, the method comprising disintegrating the microcapsules upon the topical application.

According to further features in preferred embodiments of the invention described below, the disintegrating is effectable by a rubbing or spreading action.

According to still further features in the described preferred embodiments the disintegrating is effectable by electrostatic interactions.

According to still further features in the described preferred embodiments the disintegrating is effectable by drying.

According to still further features in the described preferred embodiment the drying is effectable by heating.

According to still further features in the described preferred embodiments the composition further comprising an acceptable carrier, the disintegrating is effectable by drying and the drying is effectable by an evaporation of at least a portion of the acceptable carrier upon the topical application.

According to yet an additional aspect of the present invention there is provided a method of delivering an active ingredient from the therapeutic, cosmetic or cosmeceutic composition for topical application of the present invention the method comprising extracting the active ingredient upon the topical application.

According to further features in preferred embodiments of the invention described below, the extracting is effectable by contacting the composition with a moisture, an electrolyte, a surfactant, a buffering agent or mixtures thereof.

According to still further features in the described preferred embodiments the moisture and the electrolyte are present in a body fluid.

According to still further features in the described preferred embodiments the moisture, the electrolyte, the surfactant, the buffering agent or the mixtures thereof are added to the composition prior to the topical application.

According to still further features in the described preferred embodiments the composition further comprising an acceptable carrier and the extracting is effectable by at least a portion of the acceptable carrier.

According to still further features in the described preferred embodiments the acceptable carrier comprises a mixture of water and an auxiliary agent and the extracting is effected by the auxiliary agent after the water evaporates upon the topical application.

According to still further features in the described preferred embodiments the acceptable carrier comprises an auxiliary agent and the extracting is effectable by the auxiliary agent.

According to still further features in the described preferred embodiments the delivering of the active ingredient is time-controlled.

According to further features in preferred embodiments of the invention described below, the composition comprises two or more different types of microcapsules each of the two or more different types of microcapsules containing a different active ingredient.

According to still further features in the described preferred embodiments the composition releases/delivers each of the active ingredients at a different rate or as a result of a different action.

According to still further features in the described preferred embodiments the action is selected from the group consisting of a rubbing or spreading action, drying, contacting the microcapsules with an auxiliary agent, extraction of an active ingredient and combinations thereof.

According to still further features in the described preferred embodiments the composition comprises a first plurality of microcapsules encapsulating one or more active ingredient(s) and a second plurality of microcapsules encapsulating one or more active ingredient(s), wherein the one or more active ingredient(s) in the second plurality of microcapsules is different than the one or more active ingredient(s) in the first plurality of microcapsules.

According to still further features in the described preferred embodiments the composition further comprising a pharmaceutically, cosmetically or cosmeceutically acceptable carrier.

According to still further features in the described preferred embodiments the acceptable carrier comprises one or more non-encapsulated active ingredient(s).

According to still further features in the described preferred embodiments the one or more non-encapsulated active ingredient and the one or more active ingredient(s) are chemically reactive with one another.

According to still further features in the described preferred embodiments the acceptable carrier is selected from the group consisting of an emulsion, a cream, an aqueous solution, an oil, an ointment, a paste, a gel, a lotion, a milk, a foam, a suspension and a powder.

According to still further features in the described preferred embodiments the composition further comprising an adjuvant within the acceptable carrier.

According to still further features in the described preferred embodiments the adjuvant is selected from the group consisting of an anti-oxidant, a metal sequestering agent, a buffering agent and mixtures thereof.

According to still further features in the described preferred embodiments the acceptable carrier comprises one or more member selected from the group consisting of a thickener, an emollient, an emulsifier, a humectant a surfactant a suspending agent, a film forming agent, a foam building agent, a preservative, an antifoaming agent, a fragrance, a lower monoalcoholic polyol, a high boiling point solvent, a propellant, a colorant and a pigment.

According to still further features in the described preferred embodiments the final form of the composition is selected from the group consisting of an emulsion, a cream, an aqueous solution, an oil, an ointment, a paste, a gel, a lotion, a milk, a suspension, a powder, an aerosol, a spray, a foam, a shampoo, a hair conditioner, a lacquer, a makeup, a solid stick and a toothpaste.

According to still further features in the described preferred embodiments the one or more active ingredient(s) are selected from the group consisting of a vitamin, an anti-inflammatory agent, an analgesic, an anti-fungal agent, an anti-biotic, an anti-viral agent, an anti-acne agent, an anti histamine, an enzyme, a co-enzyme, a humectant, a dermatological agent, an insect repellent, a perfume, a color, a dye, a skin whitening agent, an aromatic oil, a flavoring agent, a dental agent and mixtures thereof.

According to still further features in the described preferred embodiments the microcapsular core further includes an adjuvant selected from the group consisting of an anti-oxidant, a metal-sequestering agent, a buffering agent and mixtures thereof.

According to still further features in the described preferred embodiments the microcapsular core is in a form of an emulsion.

According to still further features in the described preferred embodiments the emulsion is an oil-in-water emulsion.

According to till further features in the described preferred embodiments the microcapsular core is in a form selected from the group consisting of a solid, an oil solution, an aqueous solution and a dispersion.

According to still further features in the described preferred embodiments the inorganic polymer is prepared from a sol-gel precursor selected from the group consisting of a metal alkoxide monomer, a semi-metal alkoxide monomer, a metal ester monomer, a semi-metal ester monomer, a silazane monomer, a monomer of the formula $M(R)_n(P)_m$, wherein M is a metallic or a semi metallic element R is a hydrolyzable is substituent, n is an integer from 2 to 6, P is a non polymerizable substituent and m is and integer from 0 to 6, a partially hydrolyzed and partially condensed polymer thereof and mixtures thereof.

According to still further features in the described preferred embodiments the vitamin is selected from the group consisting of vitamin C, an ester of vitamin C, a salt of vitamin C and mixtures thereof, and the composition further comprising a metal sequestering agent within the microcapsular core.

According to still further features in the described preferred embodiments the metal sequestering agent is selected from the group consisting of ethylenediamine tetra acetic acid, hexamethylenediamine tetra acetic acid, ethylenediamine tetra(methylenephosphonic acid), diethylenetriamine penta(methylenephosphonic acid), or hexamethylenediamine tetra(methylene phosphonic acid), derivatives thereof salts thereof and mixtures thereof.

According to still further features in the described preferred embodiments the vitamin is a retinoid and the composition further comprising an anti-oxidant within the microcapsular core.

According to still further features in the described preferred embodiments the antioxidant is selected from the group consisting of BHT, BHA, vitamin E, vitamin E acetate, vitamin E palmitate, vitamin C, an ester of vitamin C, a salt of vitamin C and mixtures thereof.

According to still further features in the described preferred embodiments the anti-acne agent or the dental agent is a peroxide selected from the group consisting of benzyl peroxide and urea peroxide and the composition further comprising an acceptable carrier including one or more non-encapsulated active ingredient(s), whereas the non-encapsulated active ingredient is oxidized by the peroxide.

According to still further features in the described preferred embodiments the non-encapsulated active ingredient is selected from the group consisting of erythromycin, synthomycin, clindamycin, tetracycline, a retinoid, an alpha hydroxy acid, a salt thereof, a derivative thereof and mixtures thereof.

According to still further features in the described preferred embodiments the composition further comprising one or more ingredient(s) selected from the group consisting of a polymer, a fatty acid, a fatty acid derivative, a surfactant, a polysaccharide, a protein, a polypeptide, at amino acid, and a mixture thereof the ingredient is present within the microcapsular core or is attached to the microcapsular shell of the microcapsules.

According to still further features in the described preferred embodiments the dental agent is selected from the group consisting of sodium perborate, sodium percarbonate and a mixture thereof.

According to still further features in the described preferred embodiments the acceptable carrier comprises one or more auxiliary to agent(s), the auxiliary agent(s) trigger the release of the one or more active ingredient(s) from the microcapsules upon the topical application.

According to still further features in the described preferred embodiments the auxiliary agent is selected from the group consisting of a surfactant, an electrolyte, a buffering agent, a high boiling point solvent and mixtures thereof.

According to still further features in the described preferred embodiments the composition further comprising an auxiliary vehicle, the auxiliary vehicle is added to the composition prior to the topical application to trigger the release of the one or more active ingredient(s) from the microcapsules.

According to still further features in the described preferred embodiments the auxiliary vehicle comprises one or more member(s) selected from the group consisting of a surfactant, an electrolyte, a buffering agent, a high boiling point solvent and mixtures thereof.

According to still further features in the described preferred embodiments the microcapsules are designed to release the one or more active ingredient(s) upon disintegration.

According to still further features in the described preferred embodiments the disintegration is effectable by a rubbing or spreading action.

According to still further features in the described preferred embodiments the disintegration is effectable by drying.

According to still further features in the described preferred embodiments the composition is designed to release the one or more active ingredient(s) upon extraction.

According to still an additional aspect of the present invention there is provided a process for the preparation of microcapsules having a core-shell structure, wherein the core is a microcapsular core encapsulated within the shell, preferably in a form of an oil-in-water emulsion, and includes one or more active ingredient(s), whereas the shell is a microcapsular shell and includes one or more inorganic polymer(s) obtained by a sol-gel process, the process comprising preparing a hydrophobic solution or a hydrophobic dispersion comprising one or more sol-gel precursor(s) and one or more active ingredient(s) to be encapsulated within the microcapsules, emulsifying the hydrophobic solution or dispersion in an aqueous solution under high shear forces, so as to obtain an emulsion and mixing and stirring the emulsion, with a second aqueous solution, at a predetermined pH, so as to obtain the microcapsules.

According to further features in preferred embodiments of the invention described below, the emulsion is an oil-in-water emulsion and the concentration of the hydrophobic solution or dispersion in the emulsion is between 5% and 45% by weight.

According to still further features in the described preferred embodiments the diameter of the microcapsules is pre-determined by reaction conditions and/or a reaction ingredient selected from the group consisting of the shear forces, the sol-gel precursor, a composition of the aqueous solution, a composition of the second aqueous solution and combinations thereof.

According to still further features in the described preferred embodiments the hydrophobic solution or dispersion further comprises a surfactant, a polymer, a polymeric surfactant, a suspending agent or mixtures thereof.

According to still further features in the described preferred embodiments the one or more sol-get precursor(s) are selected from the group consisting of a metal alkoxide monomer, a semi-metal alkoxide monomer, a metal ester monomer, a semi-metal ester monomer, a silazane monomer, a monomer of the formula $M(R)_n(P)_m$, wherein M is a metallic or a semi metallic element. R is a hydrolyzable substituent, n is an integer from 2 to 6, P is a non polymerizable substituent and m is and integer from 0 to 6, a partially hydrolyzed and partially condensed polymer thereof and any mixture thereof.

According to still further features in the described preferred embodiments the hydrophobic dispersion is prepared by a method comprising wetting and mixing a solid active ingredient to be encapsulated within the microcapsules with one or more additive(s) selected from the group consisting of a liquid, a wetting agent and a combination thereof and micronizing the solid active ingredient by grinding or milling, so as to obtain a micronized solid active ingredient.

According to still further features in the described preferred embodiments the wetting and mixing is prior to the micronizing.

According to still further features in the described preferred embodiments the micronizing is prior to the wetting and mixing.

According to still further features in the described preferred embodiments the process further comprising adding and mixing one or more dispersing phase(s) selected from the group consisting of an oil, a sol-gel precursor and a combination thereof, so as to obtain a dispersion of the solid active ingredient in the dispersing phase.

According to still further features in the described preferred embodiments the concentration of the solid active ingredient is between about 0.001% and about 95% by weight, based on the total weight of the solid and the dispersing phase.

According to still further features in the described preferred embodiments the concentration of the solid active ingredient in the dispersion is between about 1% and about 95% by weight.

According to still further features in the described preferred embodiments the average particle size of the solid active ingredient is between about 0.1 micron and about 20 microns.

According to still further features in the described preferred embodiments the concentration of the dispersing phase in the final dispersion is between about 5% and about 99% by weight.

According to still farther features in the described preferred embodiments the liquid is selected from the group consisting of a hydrophobic liquid, a hydrophilic liquid, an aqueous liquid and mixtures thereof.

According to still further features in the described preferred embodiments the hydrophobic liquid is selected from the group consisting of an oil, a sol-gel precursor and a mixture thereof.

According to still further features in the described preferred embodiments the hydrophilic, liquid is glycerol and further wherein the aqueous liquid is water.

According to still further features in the described preferred embodiments the wetting agent is selected from the group consisting of a surfactant, a polymeric surfactant and a mixture thereof.

According to still further features in the described preferred embodiments the wetting agent is a surfactant and a concentration of the surfactant in the dispersion ranges between about 0.1% and about 20% by weight.

According to still further features in the described preferred embodiments the surfactant is selected from the group consisting of an anionic surfactant, a cationic surfactant, an amphoteric surfactant, a nonionic surfactant and mixtures thereof.

According to still further features in the described preferred embodiments the polymeric surfactant is selected from the group consisting of an anionic polymeric surfactant, a cationic polymeric surfactant an amphoteric polymeric surfactant, a nonionic polymeric surfactant and mixtures thereof.

According to still further features in the described preferred embodiments the polymeric surfactant is selected from the group consisting of a hydrocarbon-based polymer, a silicone polymer and mixtures thereof.

According to still further features in the described preferred embodiments the hydrocarbon-based polymer includes one or more ionic or non-ionic functional group(s) selected from the group consisting of a phosphate ester, a sulfate, a carboxylate, a sulfosuccinate, a sulfonate, a thiosulfonate, an amino propionate, a betaine, a phosphobetaine, an alkyl quaternary compound, an amido quaternary compound, an imidazoline quaternary compound, a carboxy quaternary compound, an alcohol aloxylate, an alkanolamide and an ester.

According to still further features in the described preferred embodiments the silicone polymer is selected from the group consisting of a silicone phosphate ester polymer, a silicone sulfate polymer, a silicone carboxylate polymer, a silicone sulfosuccinate polymer, a silicone sulfon to polymer, a silicone thiosulfate polymer, a silicone amphoteric polymer, a silicone betaine polymer, a silicone phosphobetaine polymer, a silicone alkyl quaternary polymer, a silicone quaternary polymer, a silicone imidazoline quaternary polymer, a silicone carboxy quaternary polymer, a dimethicone copolyol polymer, a silicone alkanolamide polymer, a silicone ester polymer and mixtures thereof.

According to still further features in the described preferred embodiments the oil is selected from a group consisting of mineral oil, dimethicone, cyclomethicone, alkyl siloxanes, alkylether siloxanes, dimethicone copolyols. C12-15 alkyl benzoate, isostearyl benzoate. PPG-15 stearyl ether benzoate, octyldodecyl benzoate, stearyl benzoate, methyl gluceth-20 benzoate, poloxamer 182 dibenzoate, poloxamer 105 benzoate, transcutol, bernel ester, diethylhexylmaleate, diethylhexylsebacate, diethylhaexyladipate, diisopropyladipate, diisopropylsebecate, diisopropyltnaleate, ethylhexysalicylte, tridecylsalicylate, butiloctylsalicylate, isopropylmyristate and mixtures thereof.

According to further features in preferred embodiments of the invention described below, the active ingredient is benzoyl peroxide and the composition further comprising one or more different type(s) of microcapsules, each of the one or more different type(s) of microcapsules containing one or more active ingredient(s) other than benzoyl peroxide.

According to still further features in the described preferred embodiments the active ingredient and the benzoyl peroxide are chemically reactive with one another.

According to still further features in the described preferred embodiments the one or more active ingredient(s) are selected from the group consisting of erythromycin, synthomycin, clindamycin, tetracycline, a retinoid, an alpha hydroxy acid, a salt thereof, a derivative thereof and mixtures thereof.

According to still further features in the described preferred embodiments the microcapsules are characterized as non-scratching both prior and following disintegration.

According to still further features in the described preferred is embodiments the microcapsules have an average diameter between 0.1 micron and 100 microns.

According to still further features in the described preferred embodiments the one or more inorganic polymer(s) comprise one or more organically-modified inorganic polymer(s) prepared by the sol-gel process.

According to still further features in the described preferred embodiments the amount of the one or more active ingredient(s) is between about 0.001% and about 95% by weight of the microcapsules.

The present invention successfully addresses the shortcomings of the presently known configurations by providing a composition for topical application that is designed to stabilize different active ingredients, particularly benzoyl peroxide, prior to topical application and to release the active ingredients following topical application, in a pre-determined mechanism.

BRIEF DESCRIPTION OF THE DRAWING

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION OF THE INVENTION

Figure 1:
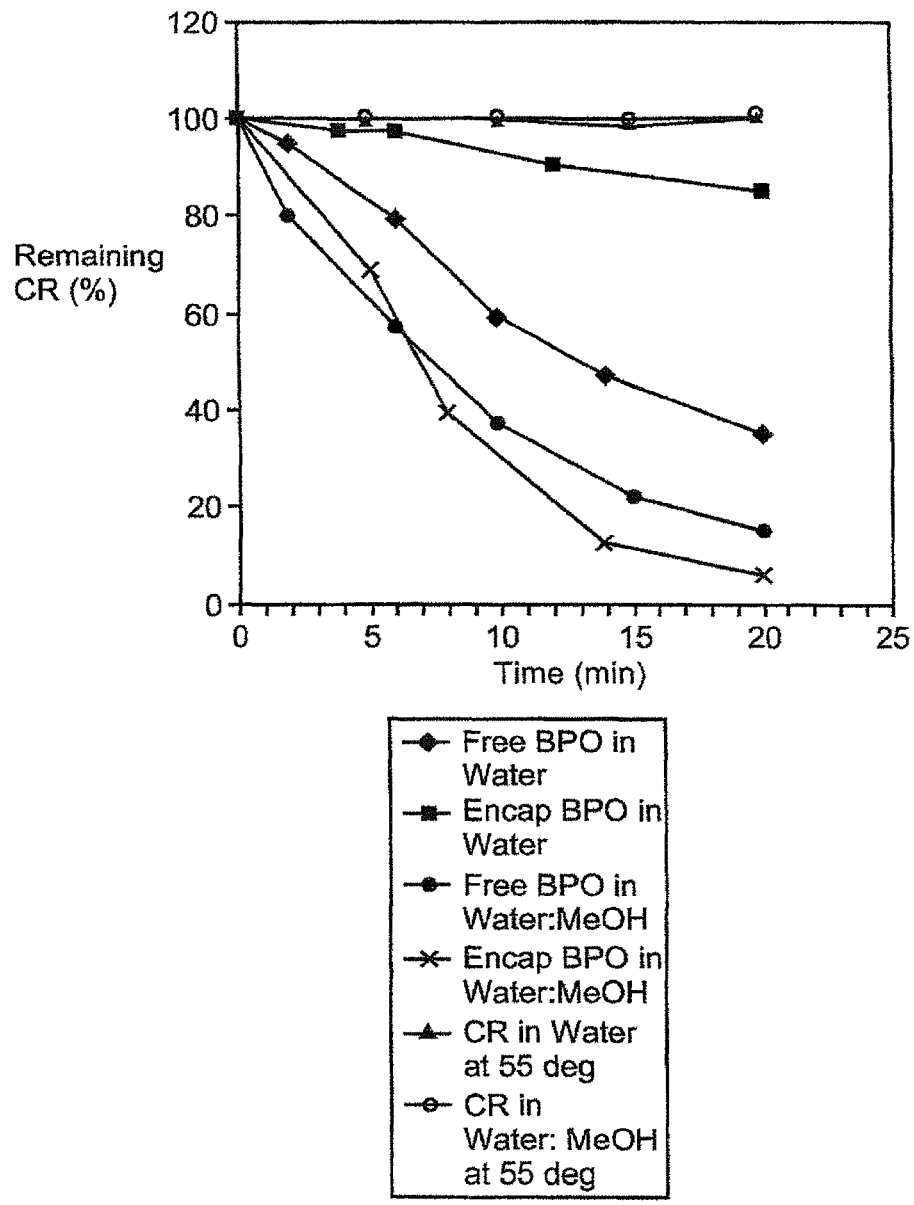
FIG. 1 is a plot illustrating the rate of oxidation of Congo Red (percents of remaining Congo Red as a function of time) in six systems tested for oxidation sensitivity, as described in Example 7 of the present invention.

The present invention is of sol-gel microcapsules that encapsulate therapeutic, cosmetic or cosmeceutic active ingredients, systems for topical application and compositions containing the active ingredients, methods of releasing, thereby delivering the active ingredients from the composition, methods of preparing the sol-gel microcapsules and a method for treating various conditions, diseases and disorders, such as ace, psoriasis and infections using the compositions. Specifically, the micro capsules and/or compositions of the present invention are designed to stabilize the encapsulated active ingredients prior to topical application and/or to release the active ingredients after topical application and thus serve as a system for enhancing the stability of the active ingredient and/or as a delivery system.

The principles and operation of the compositions, systems and methods of the present invention may be better understood with reference to to the drawings and accompanying descriptions.

Before explaining at least one embodiment of the invention in detail, it is to be understood that the invention is not limited in its application to the details of construction and the arrangement of the components set forth in the following description or exemplified by the examples. The invention is capable of other embodiments or of being practiced or carried out in various ways. Also, it is to be understood that the phraseology and terminology employed herein is for the purpose of description and should not be regarded as limiting.

According to one aspect of the present invention, there is provided a therapeutic, cosmetic or cosmeceutic composition for topical application. The composition of the present invention comprises a plurality of microcapsules that have a core-shell structure. The microcapsular core is encapsulated within the microcapsular shell and includes one or more active ingredient(s). The microcapsular shell includes one or more inorganic polymer(s) obtained by a sol-gel process.

As used herein, the phrase "active ingredient" refers to an ingredient having a therapeutic, cosmetic or cosmeceutic effect.

As used herein, the phrase "topical application" refers to an application on the skin, hair, ears, mucous membranes, rectal application, and nasal application, as well as dental or gum application within the oral cavity.

The composition of the present invention is designed to stabilize the active ingredient(s) prior to the topical application and/or to release the active ingredient(s) from the microcapsules following the topical application.

These unique properties of the composition of the present invention are highly advantageous as described hereinabove and are derived from the unique structure of the microcapsules in the composition.

While conventional microcapsules are prepared by coating the core material with organic polymers, in the present invention the core material is coated with inorganic polymers. This imparts unique properties to the microcapsule wall, such as rigidity and hence sensitivity to friction, which result in disintegration of the capsules and release of their contents, during or after topical application by various mechanisms as is further delineated hereinafter. The use of inorganic polymers for the microcapsular wall further grants the ability to control the pore size of the microcapsular shell and eliminates sensitivity of the shell to both organic solvents in the formulation and to components in the treated area.

The microcapsules of the present invention are further advantageous since they can be easily incorporated into therapeutic, cosmetic or cosmecutical compositions. Microcapsules that have a hydrophilic external surface can be dispersed in water phases, while microcapsules which have a hydrophobic external surface can be dispersed in oil phases. In both instances, simple mixing is sufficient to achieve effective dispersion.

For some applications, the microcapsules of the present invention can be designed as heat insensitive, and unless the encapsulated active ingredient is heat sensitive, they may be heated to temperatures normally used in formulation of cosmetic compositions, as is accepted in the art (for instance, up to a maximum temperature of 80° C., for up to 2 hours).

The microcapsules of the present invention are further advantageously characterized by high loading capacity of the active ingredient(s) therein.

Preferably, the load of active ingredient(s) in the microcapsules is between about 0.001% and 95% by weight of the microcapsules and, more preferably, between about 5% and 80% by weight of the microcapsules.

The character of the microcapsular core may be controlled by the process of microcapsule preparation, the percentage of active ingredient present in the core and the solubility of the active ingredient in the core. For example, a higher percentage of a solid active ingredient in the core will result in a core which is more viscous.

According to a preferred embodiment of the present invention, the microcapsular core is in the form of an emulsion, preferably an oil-in-water emulsion. An oil-in-water emulsion is highly advantageous when used in compositions for topical application since it enables the use of compositions with external water phase, which are considered to afford improved feel on the skin, and is therefore preferred in many cases over water-in-oil emulsions.

However, the microcapsular core of the present invention can be further prepared in a form of a solid, an oil solution, an aqueous solution and a dispersion.

The microcapsules of the present invention are prepared by a sol-gel process, as is further detailed hereinbelow. The sol-gel process is adaptable to different encapsulating materials such as, but not limited for, pure silica, organically-modified silica, titania, silazane, zirconia, alumina, and others, as well as combinations of the above.

Hence, the inorganic polymer in the microcapsular shell is prepared by a sol-gel process from a sol-gel precursor such as, but not limited to, metal alkoxide monomer, a semi-metal alkoxide monomer, a metal ester monomer, a semi-metal ester monomer, a silazane monomer, a monomer of the formula $M(R)_n(P)_m$, wherein M is a metallic or a semi metallic element, R is a hydrolyzable substituent, n is an integer from 2 to 6, P is a non polymerizable substituent and in is and integer from 0 to 6, a partially hydrolyzed and partially condensed polymer thereof and mixtures thereof.

According to a preferred embodiment of the present invention, the inorganic polymer includes an organically-modified inorganic polymer.

As used herein, the phrase "organically-modified inorganic polymer" refers to a polymer prepared from a sol-gel precursor of the formula $M(R)_n(P)_m$, wherein "M" is a metallic or semi-metallic element, "R" is a hydrolyzable substituent, "n" is an integer from 2 to 5, "P" is a non polymerizable substituent and "in" is an integer from 1 to 6.

The character of the microcapsular shell of the microcapsules of the present invention depends on the sol-get precursors used in the preparation of the inorganic polymer and can therefore be modified to suit the needs of a specific application, as further described herein.

The microcapsules of the present invention have an average diameter of between 0.1, micron and 100 microns. Preferably, the average diameter of the microcapsules is between 3 microns and 50 microns and, most preferably, between 8 microns and 50 microns.

In a presently preferred embodiment of the present invention, the size of the microcapsules is pre-determined in a controlled manner, as is further detailed hereinbelow. This feature has not been described in the prior art, and is of immense technical importance both in general and in the context of the present invention in particular, as is further detailed hereinbelow.

The microcapsules of the present invention are cosmetically and pharmaceutically acceptable, being smooth and optionally transparent, and large enough so that they cannot penetrate the epidermis. Furthermore, the microcapsules of the present invention are characterized, upon experiments, as non-scratching, when applied, also following disintegration thereof.

The therapeutic, cosmetic and cosmeceutic composition of the present invention comprises the microcapsules and may further comprise a pharmaceutically, cosmetically or cosmeceutically acceptable carrier.

As used herein, the term "pharmaceutically, cosmetically or cosmeceutically acceptable carrier" refers to a carrier or a diluent that does not cause significant irritation to an organism and does not abrogate the biological activity and properties of the applied active ingredient.

Examples of acceptable carriers that are useful in the context of the present invention include, without limitation, emulsions, creams, aqueous solutions, oils, ointments, pastes, gels, lotions, milks, foams, suspensions and powders.

The acceptable carrier of the present invention may include, for example, a thickener, an emollient, an emulsifier, a humectant, a surfactant, a suspending agent, a film forming agent, a foam building agent, a preservative, an antifoaming agent, a fragrance, a lower monoalcoholic polyol, a high boiling point solvent, a propellant, a colorant, a pigment or mixtures thereof.

Therefore, according to a preferred embodiment of the present invention, the final composition may be in the form of an oil, a gel, a solid stick, a lotion, a cream, a milk, an aerosol, a spray, a powder, a foam, a shampoo, a hair conditioner, a lacquer or a make-up.

The nature of the microcapsules of the present invention and the ability to control this nature, as described hereinabove, enable to design compositions for topical application which stabilize the active ingredient prior to topical application and/or release the active ingredient during or after topical application.

Hence, according to another aspect of the present invention, there is provided a system for enhancing a stability of one or more active ingredient(s) in the therapeutic, cosmetic or cosmeceutic composition for topical application of the present invention. The system comprises the microcapsules of the present invention and is designed to stabilize the active ingredient(s) prior to the topical application.

According to the present invention, the enhanced stability of the active ingredient is achieved by its encapsulation within the sol-gel microcapsules of the present invention. The encapsulation protects the active ingredient from other ingredients in the formulation and from the environment and thus extends the shelf life of the end product.

The active ingredient may be encapsulated alone or with other ingredients within the same microcapsule. Co-encapsulation of compounds that enhance stability of the sensitive ingredient is beneficial. For example, anti-oxidants can be co-encapsulated with oxygen-sensitive or oxidant-sensitive ingredients, to give "localized protection". Similarly, base-sensitive actives may be co-encapsulated with proton donating compounds that can act as a local buffer source. Acid-sensitive active ingredients can be co-encapsulated with proton acceptors, in order to protect them. Water-sensitive actives may show improved stability by encapsulation as solutes in a hydrophobic, water repelling oil. Co-encapsulating with sunscreen active ingredients, can protect light sensitive compounds. Co-encapsulation of a sensitive ingredient and a protective ingredient in one microcapsule, augments the efficacy of the protecting ingredient as both ingredients are encased together in the capsule. Moreover, by constructing such an organized system, the overall concentration of protecting ingredient, which is present in the composition, can be reduced significantly.

Since the encapsulation creates micro-domains within the entire formulation, one active ingredient can be encapsulated while a second active ingredient can be present in the carrier that surrounds the microcapsules as a non-encapsulated active ingredient. This is advantageous when the ingredients acts synergistically together, yet one is chemically reactive with the other. For example, benzoyl peroxide, retinoids and certain antibiotics are all beneficial for the treatment of acne, yet cannot be formulated together since the peroxide would oxidize the other active ingredients. Therefore, benzoyl peroxide or any other strong oxidant may be encapsulated within sol-gel microcapsules and other active ingredient(s) which are sensitive to oxidation can be present in the pharmaceutical carrier.

Alternatively, the composition or system of the present invention can include different types of microcapsules, each type encapsulating a different active ingredient. For example, one active ingredient can be encapsulated in one type of microcapsules while the other active ingredient is encapsulated in other microcapsules. The different types of microcapsules can differ only in the active ingredient encapsulated therein, to achieve enhanced stabilization of a composition that comprises active ingredients that are chemically reactive with one another. Optionally, the different types of microcapsules can differ in other characters thereof, such as their average diameter or the nature of their microcapsular shell, which can further effect the rate of releasing the active ingredients therefrom. This feature of the present invention is of immense importance, as is further discussed hereinbelow.

According to another aspect of the present invention, there is provided a system for releasing/delivering one or more active ingredient(s) from the therapeutic, cosmetic or cosmeceutic composition for topical application. The system comprises a plurality of microcapsules as described hereinabove and is designed to release the active ingredient(s) from the microcapsules following the topical application.

According to preferred embodiments of the present invention, the release of the active ingredient(s) is effected by disintegrating the microcapsules or by extracting the active ingredient(s) from the microcapsules, as is further detailed hereinbelow.

Accordingly, there are provided methods of delivering an active ingredient from the therapeutic, cosmetic or cosmeceutic composition of the present invention.

In one method, the release/delivery of the active ingredient is effected by disintegration of the microcapsules upon topical application thereof via for example sheer forces applied by a spreading action commonly used to spread creams, gels or ointments. Hence, according to a preferred embodiment of this method of present invention, the disintegration is effected by a rubbing or spreading action during or following the topical application.

In this embodiment of the present invention, the microcapsules are designed to break upon application to the skin, hair or other treated area, due to their relatively large size, e.g., 3-50 microns in diameter, which imparts a structural weakness. Friction formed upon application to the skin, is sufficient to shatter their relatively fragile shell wall. In a preferred embodiment, the thickness of the shell wall is selected to be of approximately 100 nm, which is not relatively thin; whereas the fragility of the microcapsules is due, rather, to the large diameter of the capsules.

According to another preferred embodiment of this method of the present invention, the disintegration of the microcapsules is effected by drying and/or by electrostatic interactions. Drying can be effected by heating the microcapsules, preferably at a moderate temperature such as, but not limited for, 40° C., which results in their disintegration.

Alternatively, the microcapsules of the present invention are designed to disintegrate upon application due to the nature of the carrier that surrounds them. In an example, the composition comprises the microcapsules and a water-based acceptable carrier, which has a water content of 80-99%. After topical application, drying of the microcapsules is effected by the evaporation of the water, which leaves the capsules exposed to the environment and thus triggers their disintegration.

Further alternatively, additives that are capable of maintaining humidity and moisture can be added during the preparation of the microcapsules to control the drying process. Such additives may be entrapped in the sol-gel pores or may be covalently attached to the sol-gel precursors through a non-hydrolyzable residue. Examples of such additives include polymers, fatty acids, fatty acid derivatives, surfactants, polysaccharides, proteins, polypeptides, amino acids and mixtures thereof.

Additives such as organic polymers and/or surfactants may be added during the sol-gel process to control the surface nature of the sol-gel matrix and the rate of diffusion through the pores present therein. Since the microcapsular shell may be composed of primary sot sub-micron particles, the effective pore size of the shell may be controlled by electrolytes through electrostatic interactions. This may be a trigger for release of the active ingredients.

In another method, the release/delivery of the active ingredient is effected by extraction of the active ingredient from the microcapsules upon the topical application.

In one example, the extraction is effected by contacting the composition with moisture or electrolytes. The moisture or electrolytes used in this method are present, for example, in body fluids within the sin, to sweat or sebum. The extraction can be also effected by contacting the composition with a surfactant, a buffering agent or mixtures thereof.

Alternatively, the extraction is effected by contacting the composition of the present invention with an additional composition. This additional composition comprises an auxiliary vehicle such as, but not limited for, moisture, electrolyte, surfactant, buffering agent or mixtures thereof, and is added to the composition prior to the topical application, to trigger the release of the active ingredients by extraction.

According to another preferred embodiment of this aspect of the present invention, the composition is designed such that it comprises a carrier that contains an auxiliary agent which triggers the release of the active ingredient. Examples of auxiliary agents that are useful in this context of the present invention include surfactants, electrolytes, buffering agents, high boiling point solvents and mixtures thereof.

In one example, the carrier contains high water content and a solvent having a high boiling point, in an amount of about 10% by weight of the carrier content. In this design, the release of the active ingredient is effected by the evaporation of the water upon application, which is followed by the penetration of the solvent into the microcapsular shell. The solvent dissolves and extracts the active ingredient from within the microcapsules.

The versatile mechanism of the release/delivery of the active ingredient(s), described hereinabove, provides for a pre-determinable delivery system. The timing of the release of the active ingredient(s) to following application can be pre-tailored and hence a diversified release profile can be obtained.

In one example, the composition includes microcapsules of different sizes, thicknesses and/or shell material and construction, such that the encapsulated active ingredient is released therefrom over a period of time according to any of the above described release mechanisms. Hence, the release of the active ingredient from the microcapsules can be designed to be immediate or sustained, by controlling and varying the composition and size of the microcapsular shell and/or the composition of the acceptable carrier surrounding the microcapsules.

In another example, the composition is designed such that it includes two or more different types of microcapsules, each containing a different active ingredient. Each of the active ingredient is released from the microcapsules at a different time-point following topical application, thus giving a richer therapeutic or cosmetic effect. The release of the different active ingredients in such a composition occurs at different rates or as a result of a different action.

The therapeutic, cosmetic or cosmeceutic composition of the present invention is, therefore highly beneficial for topical application of active ingredients, by being designed to stabilize and/or release the active ingredient encapsulated therein.

Particularly, the composition of the present invention is highly beneficial in cases where the active ingredients are sensitive to oxygen or other environmental components and in cases where the active ingredients are chemically reactive with one another or with other components present in the composition. The composition is further beneficial in cases where the active ingredients are skin irritating, since the encapsulation thereof accompanied by sustained release, for example, limits the concentration and time period they contact the skin, while maintaining efficacy.

Examples of active ingredients that are useful for topical application and can be beneficially encapsulated in the microcapsules of the present invention include vitamins, anti-inflammatory agents, analgesics, anti-fungal agents, antibiotics, anti-viral agents, anti-parasitic agents, anti-acne agents, humectants, dermatological agents, enzymes and co-enzymes, insect repellents, perfumes, aromatic oils, colors, dyes, skin whitening agents, flavoring agents or dental agents.

As used herein, the term "vitamins" refers to any acceptable vitamin, a derivative thereof and a salt thereof. Non-limiting examples of Vitamins include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

The phrase "dental agent" refers to a tooth whitener, a cleanser, a flavor for a toothpaste or mouthwash, a vitamin or other substance having a therapeutic effect on the teeth or oral cavity. Non-limiting examples of dental agents include bleaching agents such as urea peroxide, benzoyl peroxide, sodium perborate and sodium percarbonate.

Non-limiting examples of skin whitening agents include hydroquinone and monobenzone.

Non-limiting examples of dermatological active ingredients useful in topical applications include jojoba oil and aromatic oils such as methyl salicylate, wintergreen, peppermint oil, bay oil, eucalyptus oil and citrus oils, as well as ammonium phenolsulfonate, bismuth subgallate, zinc phenolsulfonate and zinc salicylate.

Non-limiting examples of enzymes and co-enzymes useful for topical application include co-enzyme Q10, papain enzyme, lipases, proteases, superoxide dismutase, fibrinolysin, deoxyribonuclease, trypsin, collagenase and sutilains.

Non-limiting examples, of humectants include glycerol, sodium pyroglutamate and ornithine.

Non-limiting examples of anti-inflammatory agents useful in topical application include methyl salicylate, aspirin, ibuprofen, and naproxen. Additional anti-inflammatories useful in topical applications include corticosteroids, such as, but not limited to, flurandrenolide, clobetasol propionate, halobetasol propionate, fluticasone propionate, betamethasone dipropionate, betamethasone benzoate, betamethasone valerate, desoximethasone, dexamethasone, diflorasone diacetate, mometasone furoate, amcinodine, halcinonide, fluocinonide, fluocinolone acetonide, desonide, triamcinolone acetonide, hydrocortisone, hydrocortisone acetate, fluorometholone, methylprednisolone, and prednicarbate.

Non-limiting examples of anti-infectious and anti-acne agents include benzoyl peroxide, sulfur, resorcinol and salicylic acid.

Not-limiting examples of antifungal agents include miconazole, clotrimazole, butoconazole, fenticonasole, tioconasole, terconazole, sulconazole, fluconazole, haloprogin, ketonazole, ketoconazole, oxinazole, econazole, itraconazole, terbinafine, nystatin and griseofulvin.

Non-limiting examples of antiviral agents include famciclovir, valcyclovir and acyclovir.

Non-limiting examples of antibiotics include erythromycin, clindamycin, synthomycin, tetracycline, metronidazole and the likes.

Non-limiting examples of anti-parasitic agents include scabicedes, such as permethrin, chromatin, lindane and ivermectin.

Non-limiting examples of antihistamines include chlorpheniramine, brompheniramine, dexchlorpheniramine, triprolidine, clemastine, diphenhydramine, promethazine, piperazines, piperidines, astemizole, loratadine and terfenadine.

Non-limiting examples of local anesthetics include benzocaine, butamben, butamben piorate, cocaine, procaine, tetracaine, lidocaine and pramoxine hydrochloride.

Non-limiting examples of chemotherapeutic agents include 5-fluorouracil, masoprocol, mechlorethamine, cyclophosphamide, vincristine, chlorambucil, streptozocin, methotrexate, bleomycin, dactinomycin, daunorubicin, coxrubicin and tamoxifen.

Compositions for topical application typically comprise, in addition to therapeutic active ingredients, other ingredients such as flavoring agents, insect repellents, fragrances, colors and dyes. These ingredients often cause complications when formulated in such compositions.

For example, fragrances have no therapeutic action, yet they often cause skin irritation. Entrapment of fragrances may thus serve to decrease skin sensitivity to fragrances, while extending their effectiveness period through sustained release.

Colors and dyes are also typically incompatible with formulation ingredients. Thus, using the compositions and methods of the present invention, they can be protected by encapsulation and released upon application.

Examples of flavoring agents are methyl salicylate and peppermint oil, which can be formulated, for example, within a composition useful for dental application.

Non-limiting examples of insect repellents include pediculicides for treatment of lice, such as pyrethrins, permethrin, malathion, lindane and the likes.

According to preferred embodiments of the present invention, the therapeutic, cosmetic or cosmeceutic composition further comprises an adjuvant.

As used herein, the term "adjuvant" refers to a material used in conjunction with the active ingredient to preserve the stability of the active ingredient within the composition.

The adjuvant can be encapsulated with the active ingredient within the microcapsular core, as described hereinabove, or be present in the acceptable carrier that surrounds the microcapsules. The adjuvant may further serve to preserve the stability of non-encapsulated active ingredients within the carrier.

Typical adjuvants according to the present invention include, for example, anti-oxidants, metal sequestering agents, buffering agents and mixtures thereof.

In one example, a metal sequestering agent is used as an adjuvant encapsulated together with vitamin C.

The encapsulated metal sequestering agent in this case can be, for example, ethylenediamine tetra acetic acid, hexamethylenediamine tetra acetic acid, ethylenediamine tetra(methylenephosphonic acid), diethylenetriamine penta(methylenephosphonic acid), or hexamethylenediamine tetra(methylene phosphonic acid), derivatives thereof, salts thereof and/or mixtures thereof.

In another example, an anti-oxidant is encapsulated as an adjuvant together with a retinoid. The antioxidant can be, for example, BHT, BHEA, vitamin E, vitamin E acetate, vitamin E palmitate, vitamin C, an ester of vitamin C, a salt of vitamin C and/or mixtures thereof.

As used herein, the term "BHT" refers to butylated hydroxy toluene.

As used herein, the term "BHA" refers to butylated hydroxy anisole.

As the composition of the present invention is beneficial for topical application of a wide variety of active ingredients, it can be efficiently used in the treatment of various disorders and conditions.

Thus, according another aspect of the present invention there is provided a method of treating a skin, hair, ear, mucosal membrane, rectal, nasal or dental condition in a subject in need thereof. The method is effected by topically applying the composition of the present invention onto the area to be treated.

Non-limiting examples of the conditions, diseases or disorders that are treatable by the method of the present invention include, for example, acne, psoriasis, seborrea, bacteria, virus or fungus infections, inflammatory process, aging signs, dandroofs and cavity.

In one preferred embodiment of the present invention, the therapeutic, cosmetic or cosmeceutical composition employed includes a peroxide such as, but not limited to, benzoyl peroxide as the encapsulated active ingredient.

As used herein, the term "peroxide" refers to an organic compound containing an oxygen-oxygen bond capable of cleaving and forming oxygen free-radicals. The peroxides include peroxyacids of carboxylic acids, peroxyesters of carboxylic acids and the dimeric product of carboxylic peroxyacids. Exemplary peroxides include t-butyl peroxyesters of straight and branched chain aliphatic carboxylic acids, and dimeric peroxides such as lauroyl peroxide and benzoyl peroxide.

As described hereinabove, benzoyl peroxide is a highly reactive active ingredient which is presently used mainly as an antibacterial and antimicrobial agent in the treatment of acne or as an antibacterial and bleaching agent in toothpaste and other compositions designed for oral cavity/dental applications. In most of the presently known formulations for topical application, the benzoyl peroxide serves as an active ingredient that reacts synergistically with other active ingredients such as antibiotics and retinoids. However, these other active ingredients are easily oxidized by the benzoyl peroxide and therefore the production, storage and use of the formulations containing these ingredients is limited. Furthermore, since benzoyl peroxide is highly reactive per se, and therefore unstable and tends to cleave exothermically even at room temperature, the formulations thereof often include ingredients designed to stabilize the peroxide prior to its application.

Enhanced stability of benzoyl peroxide, according to the present invention, is obtained by its encapsulation within the microcapsules of the present invention. The benzoyl peroxide is present in the microcapsular core, preferably as an oil-in-water emulsion or as a solid-in-oil-in-water emulsion, and is encapsulated by the microcapsular shell. The microcapsular shell protects the benzoyl peroxide from contacting the environment and thus reduces its, reactivity and/or sensitivity. The microcapsular shell further protects the benzoyl peroxide from reacting with other active ingredients in the composition, as described hereinabove.

The release or delivery of the benzoyl peroxide from the microcapsules is effected by the systems and methods described hereinabove. Since the systems and methods of the present invention are designable for controlled release of the active ingredients, they enable, if so required, a controlled, sustained release of the benzoyl peroxide from the microcapsules. This, in turn, is beneficial because benzoyl peroxide is a very reactive chemical.

According to another aspect of the present invention, there is provided a method of treating a skin or dental condition in a subject in need thereof, which is effected by topically applying the benzoyl peroxide containing composition of the present invention onto the area to be treated, which can be, used in the treatment of a variety of skin conditions, such as acne, psoriasis, seborrea, bacteria, virus or fungus infection and inflammatory process and in the treatment of dental conditions such as cavities or as a bleaching agent.

According to yet another aspect of the present invention there is provided a process of preparing the sol-gel microcapsules of the present invention. The process comprises preparing a hydrophobic solution or a hydrophobic dispersion that comprises one or more sol-gel precursor(s) and one or more active ingredient(s) to be encapsulated within the microcapsules; emulsifying the hydrophobic solution or dispersion in an aqueous solution under high shear forces, so as to obtain an emulsion; and mixing and stirring the emulsion, with a second aqueous solution, at a predetermined pH, so as to obtain microcapsules having a core including the active ingredient and a shell encapsulating same.

According to still another aspect of the present invention, the process described hereinabove is utilized to prepare sol-gel microcapsules which include a microcapsular core in a form of an oil-in-water emulsion. The preparation of such microcapsules is highly beneficial when used in compositions for topical application, as is further described hereinabove.

According to a preferred embodiment of the present invention, the concentration of the hydrophobic solution or dispersion in such an oil-in-water emulsion is between 5% and 45% by weight.

Thus, in a presently preferred embodiment, the process of the present invention includes, as a first step, the preparation of a hydrophobic solution or dispersion of the active ingredient(s). The active ingredients that are useful in the present invention are typically oil-soluble, and therefore they are first dissolved in the sol-gel precursor(s) and optionally in one or more oil(s), to form a hydrophobic solution. Alternatively, active ingredients that do not dissolve in a hydrophobic liquid may be encapsulated as a dispersion, by first dispersing in a suitable oil, which is miscible with the sol-gel precursor, prior to dissolving in the sol-gel precursor.

The hydrophobic solution or dispersion may further comprise a surfactant, a polymer, a polymeric surfactant, a suspending agent or mixtures thereof.

When the active ingredient to be encapsulated is a solid, the processes of the present invention further includes steps for preparing a hydrophobic dispersion. These steps are effected by wetting and mixing the solid active ingredient with one or more additive(s) and micronizing the solid active ingredient, so as to obtain a micronized solid active ingredient.

According to one approach, the hydrophobic dispersion is prepared by first wetting and mixing a solid ingredient to be encapsulated with one or more additive(s) such as, but not limited to, liquids, wetting agents or a combination thereof. The wetted solid obtained is then micronized by grinding, milling or optionally ultrasound, to obtain a dispersion of the solid within the additive(s). The micronizing is effected by employing, for example, a roller mill, a ball mill, a colloid mill a high-pressure mill or a high-shear mill. The milling or grinding is continued, until a dispersion of the active ingredient at the desired particle size is obtained within the liquid phase.

The liquid used in the wetting procedure includes a hydrophobic liquid, a hydrophilic liquid, an aqueous liquid or a combination thereof.

The hydrophobic liquid may include, for example, an oil or a sol-gel precursor.

The wetting agent used in the wetting procedure includes, for example, a surfactant, a polymeric surfactant or mixtures thereof. Alternatively, glycerol, water or organic solvents may also be used in the wetting procedure.

When the wetting agent is a surfactant, the concentration of the surfactant in the dispersion preferably ranges between about 0.1% and about 20% by weight, preferably between 1% and 10% by weight.

Non-limiting examples of surfactants that are useful in the context of this aspect of the present invention include anionic surfactants, cationic surfactants, amphoteric surfactants, non-ionic surfactants and mixtures thereof.

Non-limiting examples of polymeric surfactants that are useful in the context of this aspect of the present invention include anionic polymeric surfactants, cationic polymeric surfactants, amphoteric polymeric surfactants, nonionic polymeric surfactants and mixtures thereof. Additional examples of polymeric surfactants include hydrocarbon-based polymers, silicone polymers and mixtures thereof.

Non-limiting examples of hydrocarbon-based polymers that are useful in the context of this aspect of the present invention include hydrocarbon-based polymers having one or more ionic or non-ionic functional group(s) such as, but not limited to, a phosphate ester, a sulfate, a carboxylate, a sulfosuccinate, a sulfonate, a thiosulfonate, an amino propionate, a betaine, a phosphobetaine, an alkyl quaternary compound, an amido quaternary compound, an imidazoline quaternary compound, a carboxy quaternary compound, an alcohol aloxylate, an alknolamide and an ester.

Non-limiting examples of silicone polymers that are useful in the context of this aspect of the present invention include a silicone phosphate ester polymer, a silicone sulfate polymer, a silicone carboxylate polymer, a silicone sulfosuccinate polymer, a silicone sulfonate polymer, a silicone thiosulfate polymer, a silicone amphoteric polymer, a silicone betaine polymer, a silicone phosphobetaine polymer, a silicone alkyl quaternary polymer, a silicone quaternary polymer, a silicone imidazoline quaternary polymer, a silicone carboxy quaternary polymer, a dimethicone copolyol polymer, a silicone alkanolamide polymer, a silicone ester polymer and mixtures thereof.

According to another approach, the hydrophobic dispersion is prepared is a reversed order by first micronizing the solid ingredient, as described hereinabove, and then wetting and mixing the micronized solid with one or more additive(s), as described hereinabove.

Both methods may further benefit from adding a dispersing phase. The dispersing phase may be added during each of the steps employed, e.g., during the wetting, during the micronizing or both. The dispersion phase may include, for example, an oil, a sol-gel precursor or a combination thereof.

When the process employs high concentrations of the solid active ingredient, so as to obtain a high load of the active ingredient in the microcapsules, the amount of oil used in the wetting stage is sufficient and no additional quantity of oil is desired at any later stage, to form the final dispersion. In this case, the dispersion formed in the wetting step is a highly concentrated slurry.

Non-limiting examples of oils that are useful in the context of this aspect of the present invention include mineral oil, dimethicone, cyclomethicone, alkyl siloxanes, alkylether siloxanes, dimethicone copolyols. C12-15 alkyl benzoate, isostearyl benzoate. PPG-15 stearyl ether benzoate, octyldodecyl benzoate, stearyl benzoate, methyl gluceth-20 benzoate, poloxamer 182 dibenzoate, poloxamer 105 benzoate, transcutol, bernel ester, diethylhexylmaleate, diethylhexylsebacate, diethylhexyladipate, diisopropyladipate, diisro pysebacate, diisopropymaleate, ethylhexylsalicylate, tridecylsatloylate, butiloetylsalicylate, isopropylmyristate and mixtures thereof.

Preferably, the concentration of the solid active ingredient, to be encapsulated as a dispersion in the microcapsular core of the microcapsules, is between about 1% and 95% by weight of the final dispersion, as measured immediately before emulsification under high shear force. Most preferably, this concentration is between 20% and 50% by weight of the microcapsules.

Further preferably, the concentration of the solid active ingredient prior to emulsification is between about 0.001% and about 95% by weight, based on the total weight of the solid and the dispersing phase. More preferably it is between 40% and 90%.

Further preferably, the concentration of the dispersing phase in the final dispersion is between about 5% and about 99% by weight.

The preferred concentration of the oil at this point, prior to emulsification, is between about 5% and about 99% by weight, most preferably between 10% and 40% by weight.

Preferably, the concentration of the sol-gel precursors in the dispersion immediately prior to emulsification, is between about 5% and about 99% by weight, preferably between 20% and 60% by weight.

The particle size of the dispersed solid is preferably between about 0.1 micron and 20 microns, more preferably between 0.2 micron and 2 microns.

The sol-gel precursors used in the processes of the present invention can be selected from metal or semi-metal alkoxide monomers, metal ester monomers, silazane monomers, semi-metal ester monomers or monomers of the formula $M(R)n(P)m$, wherein "M" is a metallic or semi metallic element, "R" is a hydrolyzable substituent, "n" is an integer from 2 to 6, "P" is a non polymerizable substituent and "m" is an integer from 0 to 6. Alternatively, a partially hydrolyzed and partially condensed polymer thereof may be used, or any mixture thereof.

In a preferred embodiment of the present invention, the sol-gel microcapsules are silica or organically-modified silica microcapsules. The term "organically-modified silica microcapsules" refers to sol-gel microcapsules which are obtained when the sol-gel precursors are of the formula $M(R)_n(P)_m$, wherein "M" is Si, "R" is a hydrolyzable substituent, "n" is an integer from 2 to 5, "P" is a non polymerizable substituent and "m" is an integer from 1 to 6.

Based on the nature of the active ingredient undergoing encapsulation, the processes described herein are performed under conditions chosen so as to protect the active ingredient from decomposition, e.g., inert atmosphere, protection from light, reaction in the presence of oxygen scavengers or metal ion sequestering agents, etc.

The microcapsules obtained by the processes of the present invention have an average diameter between 0.1 micron and 100 microns. The diameter of the microcapsules can be predetermined by proper selection of reaction ingredients and/or reaction conditions. Reaction conditions that may affect the diameter of the microcapsules include, for example, the shear forces, the temperature and the pressure applied during the process. Reaction ingredients that may affect the diameter of the microcapsules include, for example, ingredients that affect properties such as surface tension, specific gravity, viscosity, hydrophilicity/hydrophobicity, solubility and ionic strength of the solutions, dispersions and/or emulsions obtained through the process. Such ingredients include, for example, the sol-gel precursor, as well as the surfactants, polymers and other additives that are added during the process to the solutions, dispersions and/or emulsions as described hereinabove and are known in the art to affect these properties.

Conditions and ingredients that may affect the wall thickness of the microcapsular shell of the microcapsules of the present invention include, for example, the sol gel precursor, the catalyst(s), the concentrations of both the reactants and the surfactants, polymers and other additives that are added during the process, the concentration ratios of the reactants and these additives, the temperature and pressure applied during the process, the reaction time and the mode of stirring and mixing.

Conditions and ingredients that may affect the stability of the microcapsules include, for example, the final form of the obtained microcapsules, e.g., as a dispersion or as a dry powder, the pH and various ingredients that are added during the process such as polymers, surfactants, preservatives, viscosity modifiers, additional solvents and ions.

The final form of a product manufactured in accordance with the teachings of the present invention can be a dry powder containing free-flowing microcapsules. A dry powder is obtained, despite the fact that the microcapsules themselves enclose up to 95% by weight of oils.

According to a preferred embodiment of the present invention, the processes of the present invention are utilized to prepare sol-gel microcapsules that encapsulate benzoyl peroxide.

In these processes, the benzoyl peroxide can be dissolved in a suitable oil, so as to obtain the hydrophobic solution as described hereinabove. Alternatively, a hydrophobic dispersion of benzoyl peroxide can be prepared according to any of the methods described hereinabove.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Encapsulation of Methyl Salicylate in Silica

Methyl salicylate is useful as a topical anti-inflammatory agent, and as a flavoring agent in dental care products.

33 grams of methyl salicylate were mixed with 33 grams tetraethoxysilane (TEOS). The organic phase was emulsified in 300 grams as of aqueous solution containing 1% acetyltrimethyl ammonium chloride (CTAC) under high shear. The vessel walls were cooled by immersion in an ice-water bath during the homogenizing process. This emulsion was then poured into an IKA LR-A 1000 Laboratory reactor, equipped with Eurostar Power control-vise. P4 stirrer, containing 300 grams NaOH aqueous solution at pH 11.5. The solution was stirred at 200 rpm. After 7 days the product was precipitated in a centrifuge. The final product was re-suspended in water containing 1% polyvinyl pyrrolidone to receive a suspension containing 32.4% methyl salicylate encapsulated in silica particles of 0.5 to 10 micron.

Example 2

Encapsulation of Methyl Salicylate and Oleic Acid in Silica

Methyl salicylate degrades through hydrolysis in a basic environment. To protect it from hydrolysis it is co-encapsulated with oleic acid.

8.25 grams methyl salicylate were mixed with 24.25 grams oleic to acid. 33 grams TEOS were added to the mixture. This oil phase was emulsified and the emulsion was poured into a basic solution of pH 11.5. The mixture was stirred at 50 to 240 rpm. After 3 days, 6.4 grams of $MgSO_4$ were added to 440 grams of the resulting suspension. The mixture was stirred for 1 hour, and thereafter allowed to settle for 2 hours. It was then filtered using a Whatman No. 40 filter. The product was obtained as paste containing 5.6% methyl salicylate.

Example 3

Encapsulation of Erythromycin in Silica

Combinations of erythromycin and benzoyl peroxide are useful in the treatment of acne but usually must be formulated as a two component system, because of incompatibility of the two active ingredients.

1.7 grams erythromycin was mixed with 14.9 grams octylmethoxy cinnamate. 19.5 grams TEOS were added to the mixture. This oil phase was emulsified and the emulsion was poured into a basic solution of pH 11.5. The mixture was stirred at 50 to 240 rpm. Flocculation was induced by the addition of $MgSO_4$ at a final concentration of 0.1% by weight. The precipitate was collected by filtration with a Whatman No. 40 paper. The product was obtained as a paste, with a particle size distribution of 1-12 microns (an average size of 6.2 microns).

Example 4

Encapsulation of Dissolved Benzoyl Peroxide in Silica

Benzoyl peroxide is useful as a topical anti-acne agent.

30 grams of 6% (w/w) benzoyl peroxide (BPO) in diisopropylsebacate ester were mixed with 20 grams of TEOS. The organic phase was emulsified in 200 grams of an aqueous solution containing 1% CTAC under high shear. The vessel walls were cooled by immersion in an ice-water bath during the homogenizing process. This emulsion was then poured into an IKA LR-A 1000 Laboratory reactor, equipped with Eurostar Power control-visc P4 stirrer, containing 200 grams NaOH aqueous solution at pH 10. The solution was stirred at 200 rpm. After 3 days the product was separated by filtration with a Whatman No. 40 paper and washed. The final product was re-suspended in water to obtain a dispersion containing a 4% benzoyl peroxide encapsulated in silica particles of 0.5-15 microns.

Example 5

Encapsulation of Dispersed Benzoyl Peroxide in Silica 32.5 grams of micronized benzoyl peroxide containing 25% water (w/w) were dispersed by a Polytron homogenizer in a solution containing 1 gram silicon emulsifier (Abil EM90. Goldschmit), 5 grams volatile silicon oil (Dow Corning 200® Fluid, 0.65 cst) and 11.5 grams TEOS. The dispersion obtained was poured into 200 grams of an aqueous solution containing 1% CTAC under mild stirring conditions using a conventional propeller agitator. The solid-oil-water (s/o/w) emulsion obtained was then to poured into an IKA LR-A 1000 Laboratory reactor, equipped with Eurostar Power control-visc P4 stirer, containing 200 grams NaOH aqueous solution at pH 10. The solution was stirred at 200 rpm. After 3 days the product was separated by filtration and washed. The final product was re-suspended in water to obtain a dispersion containing a 35% benzoyl peroxide encapsulated in silica particles of 0.5-50 micros.

Example 6

Encapsulation of Dissolved Benzoyl Peroxide in Silica 60 grams of 78% (w/w) benzoyl peroxide (BPO) in dipropyleneglycol dibenzoate were mixed with 40 grams of TEOS. The organic phase was emulsified in 400 grams of an aqueous solution containing 1% CTAC under high shear forces. The vessel walls were cooled by immersion in an ice-water bath during the homogenization process. This emulsion was then poured into an IKA LR-A 1000 Laboratory reactor, equipped with Eutostar Power control-vise P4 stirrer, containing 400 grams NaOH aqueous solution at pH 10. The solution was stirred at 200 rpm. After 3 days the product was separated and washed. The final product was resuspended in water with a final concentration of 4-6% BPO encapsulated within silica particles of 0.5 r 5 microns.

Example 7

Stabilization of Oxidation-Sensitive Compounds Via Encapsulation of Benzoyl Peroxide Combinations of benzoyl peroxide and oxidation-sensitive active ingredients such as retinoids and antibiotics are highly useful in formulations for the treatment of acne, and therefore encapsulation of benzoyl peroxide can facilitate obtaining a stable formulation containing both ingredients.

The azo dye Congo Red (CR) was used as a model for oxidation-sensitive compound in oxidation sensitivity experiments performed with encapsulated BPO.

Six comparative systems were utilized in these experiments. Two liquid vehicles were used: water, which prevents BPO solubility in the external dispersing phase of the capsules, and a solution of 50% methanol in water which promotes BPO solubility.

In the first system, 9 grams of a silica dispersion prepared as described under Example 4, containing 4% (w/w) encapsulated benzoyl peroxide and 9 grams of water, were stirred in a 25 ml beaker with a magnetic stirrer.

In the second system, 9 grams of aqueous dispersion containing 4% (w/w) free benzoyl peroxide suspended with 0.9% CTAC (w/w) and 0.1% TWEEN 20 (w/w) and 9 grams water were stirred in a 25 ml beaker with a magnetic stirrer.

The third system was a blank solution for the experiment, and was prepared by stirring 0.9% CTAC (w/w), 0.1% TWEEN 20 (w/w) and 9 grams water in a 25 ml beaker with a magnetic stirrer.

In the fourth system, 9 grams of a silica dispersion prepared as described under Example 4, containing 4% (w/w) encapsulated benzoyl peroxide and 9 grams of a 50% (w/w) methanol solution in water were stirred in a 25 ml beaker with a magnetic stirrer.

In the fifth system, 9 grams aqueous dispersion containing 4% (w/w) free benzoyl peroxide suspended with 0.9% CTAC (w/w) and 0.1% TWEEN 20 (w/w) and 9 grams of a 50% (ww) methanol solution in water were stirred in a 25 ml beaker with a magnetic stirrer.

The sixth system was a blank for the experiment, and was prepared by stirring 0.9% CTAC (w/w) and 0.1% TWEEN 20 (w/w) and 9 grams of a 50% (w/w) methanol solution in water in a 25 ml beaker with a magnetic stirrer.

Following a mixing period of 30 minutes, the temperature at each system was raised to 50-55° C. and 2 ml of a 0,02% (w/w) aqueous solution of CR solution were added to each system at time 0. After stirring the suspension for 1 minute, a sample of 1.5 to 2 ml was taken from the suspension and filtered through a 0.2-micron cut-off hydrophilic filter into an absorption cell of a spectrophotometer. The absorption spectrum of each sample was assessed covering a range of 200-700 nm wavelengths. A series of five to eight additional spectral measurements were performed for each system at various times utilizing the same method.

An absorption shift for the $\lambda_{max}$ of CR in the different investigated systems was observed as compared to its spectrum in water alone ($\lambda_{max}$ in water is 497 an), due to the presence of the surface active agents TWEEN 20 (509 nm) and CTAC (470 nm). Therefore, each system was followed at its respective 7.

As is shown in FIG. 1, systems containing free or solubilized benzoyl peroxide revealed effective oxidation of CR, with much of the CR depleted from the solution. The percent of remaining CR in solution after 20 minutes in systems 2, 4 and 5 were 35%, 15% and 5%, respectively, as compared to 100% for both blanks (systems 3 and 6). Encapsulated BPO, however, revealed low depletion, i.e., 92% remaining CR. These results indicate that benzoyl peroxide can be effectively encapsulated in sol-gel microcapsules such that the microcapsule shell behaves as an isolation barrier from co-formulated oxidation-sensitive compounds. It is also concluded that BPO preserves its activity in the encapsulated state as its release via extraction nevertheless shows oxidative capacity, as seen in system 5 (FIG. 1).

Example 8

Release of Encapsulated Material Via Capsule Drying

An encapsulated sunscreen compound, octylmethoxy cinnamate (OMC), prepared as described in U.S. Pat. No. 6,238, 650 was used as a model in this example. In order to simulate physiological conditions of the epidermis, passage of OMC released from silica capsules through a polysulfone membrane into a glass cell was followed as a function of time.

Hydrophobic Tuffryn® membranes were pretreated with isopropyl myristate and each membrane was placed over the opening of a glass cell (a horizontal Franz-type cell). The area of each membrane was 1.3 cm². The upper side of the membrane was exposed to the air. A suspension of silica-encapsulated OMC was applied to the upper side of the membrane. The underside of the membrane faced the contents of the glass cell, which held approximately 3.5 ml of a 4% (w/v) bovine serum albumin (BSA) in PBS, at pH 7.4, at a temperature of 35° C. The PBS-BSA solution was continuously stirred with Teflon-coated magnets.

A suspension of microcapsules containing 8.8% OMC (octylmethoxy cinnamate) was gently applied over each membrane and spread evenly on its upper surface. One membrane was loaded with 0.4 ml/cm² OMC suspension, while the second membrane was loaded with 0.005 ml/cm² of OMC suspension.

At several time points over a period of 22 hours, a sample of 200 μl was removed from the solution in the cell and analyzed using HPLC to determine the amount of OMC that was released from the microcapsules and passed through the membrane into the glass cell. After each sample removal, an equal volume (i.e., 200 μl) of fresh solution was returned to the cell.

Cumulative receptor concentration-time profiles were then plotted and used to compare the effect of concentration on passage through the membrane.

Tables 1 and 2 below show the amount of OMC present in a sample taken from the cell below the membrane after passage through a membrane loaded with 0.005 ml/cm² (Table 1) and through a membrane loaded with 0.4 ml/cm² (Table 2), as measured by HPLC in units of μg/cell.

Figure 2:
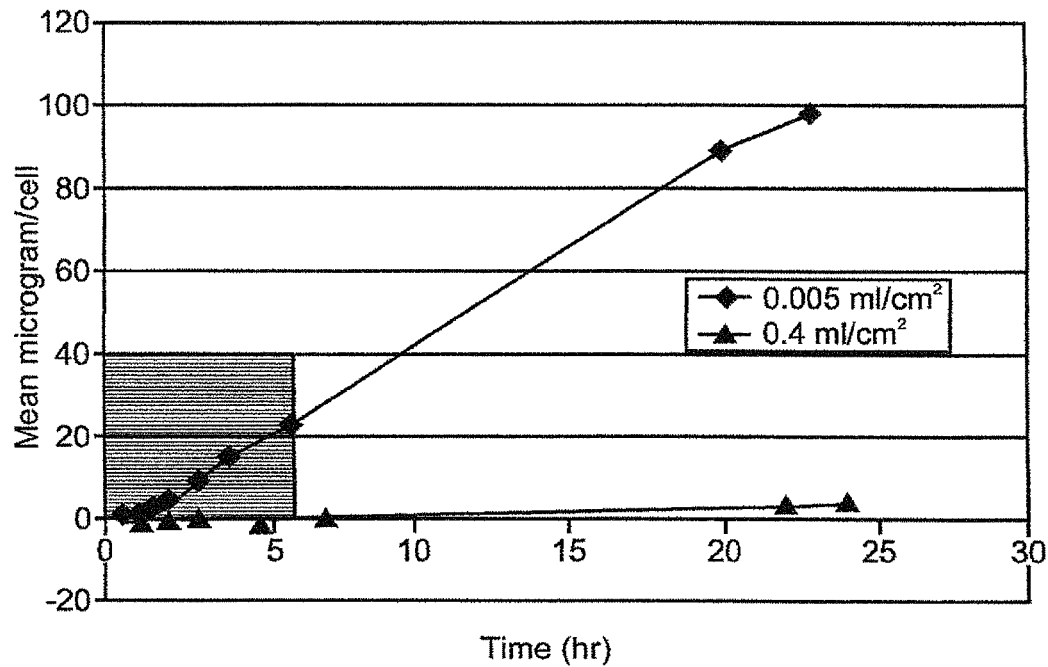
FIG. 2 is a graph illustrating the amount of octylmethoxy cinnamate (OMC) released from a suspension of microcapsules encapsulating OMC, over a period of 22 hours according to the present invention.
Figure 3:
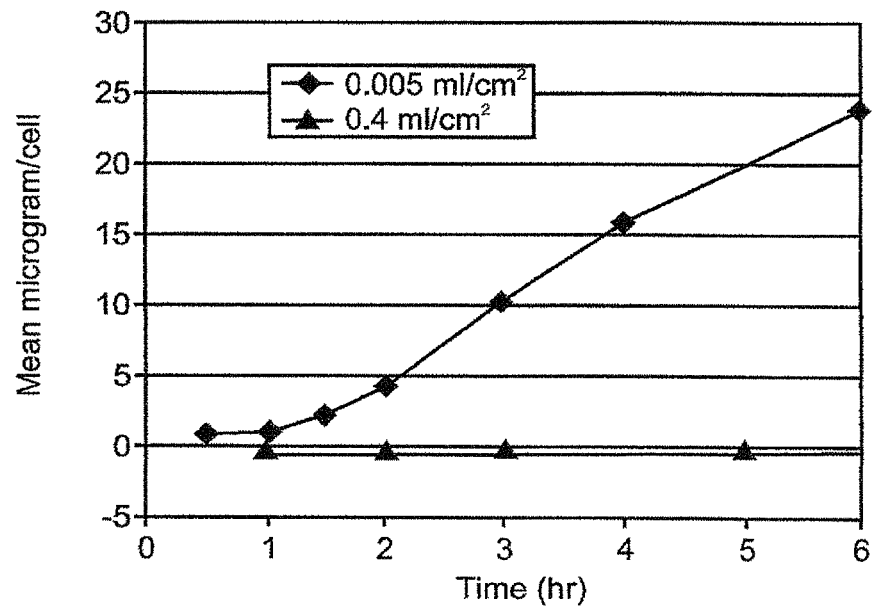
FIG. 3 is a graph illustrating the amount of OMC released during the first six hours, from a suspension of microcapsules encapsulating OMC according to the present invention.

The obtained results are further presented in FIG. 2, which plots the results in graph format, and highlighted in FIG. 3, which shows the first six hours of the experiment (FIG. 3 represents an enlargement of the gray area in the lower left-hand corner of FIG. 2).

As was detected in the withdrawn samples, after 1.5 hours, the OMC was released at significantly increasing amounts through the membrane loaded with 0.005 m/cm² of OMC, while no significant amount of OMC was detected throughout all time-points of the experiment for samples withdrawn from the cell underneath the membrane loaded with the higher dose of 0.4 ml/cm². These results indicate that no appreciable release of OMC through the membrane occurred. This is contrary to the expectation, as the higher dose of 0.4 ml/cm² contains about 80 times more OMC as compared to the lower dose of 0.005 ml/cm². These paradoxical results can be understood, if the release of OMC from within the microcapsules is triggered by total evaporation of the water content, from the silica suspension. In the case of 0.005 ml/cm², the amount of water is minimal, and the suspension is highly exposed to the air above the membrane, and thus, subject to evaporation. The total evaporation of water leads to drying of the silica pores, which results in release of the encapsulated matter. This drying does not occur in the higher dose of 0.4 ml/cm², therefore the capsules retain their contents, and no OMC is passed through the membrane. Tailoring of the formulation of the carrier surrounding the microcapsules, to induce certain drying rates can therefore be used as a mechanism of controlled release of the encapsulated material.

TABLE 1

| Time (hours) | Sample 1 (μg/cell) | Sample 2 (μg/cell) | Sample 3 (μg/cell) | Mean data ± SEM (μg/cell) |
|---|---|---|---|---|
| 0.5 | 0.5 | 0.4 | 0.6 | 0.5 ± 0.0 |
| 1 | 1.0 | 0.5 | 0.6 | 0.7 ± 0.1 |
| 1.5 | 3.6 | 0.9 | 0.7 | 1.8 ± 0.9 |
| 2 | 7.5 | 3.3 | 2.1 | 4.3 ± 1.6 |
| 3 | 15.9 | 8.4 | 6.6 | 10.3 ± 2.8 |
| 4 | 20.8 | 14.1 | 12.6 | 15.8 ± 2.5 |
| 6 | 28.7 | 22.2 | 21.2 | 24.0 ± 2.3 |
| 20 | 61.3 | 96.7 | 109.1 | 89.0 ± 14.3 |
| 23 | 66.8 | 106.0 | 121.7 | 98.1 ± 16.3 |

TABLE 2

| Time (hours) | Sample 1 (μg/cell) | Sample 2 (μg/cell) | Sample 3 (μg/cell) | Mean data ± SEM (μg/cell) |
|---|---|---|---|---|
| 1 | −0.5 | −0.5 | −0.5 | −0.5 ± 0.0 |
| 2 | −0.5 | −0.5 | −0.5 | −0.5 ± 0.0 |
| 3 | −0.5 | −0.5 | −0.4 | −0.4 ± 0.0 |
| 5 | −0.3 | −0.4 | −0.2 | −0.3 ± 0.1 |
| 7 | −0.1 | −0.3 | −0.1 | −0.1 ± 0.1 |
| 22 | 5.3 | 1.5 | 1.9 | 2.9 ± 1.2 |
| 24 | 6.1 | 1.6 | 2.1 | 3.3 ± 1.4 |

Example 9

Release of BPO from Microcapsules by Rubbing Action

Figure 4A:
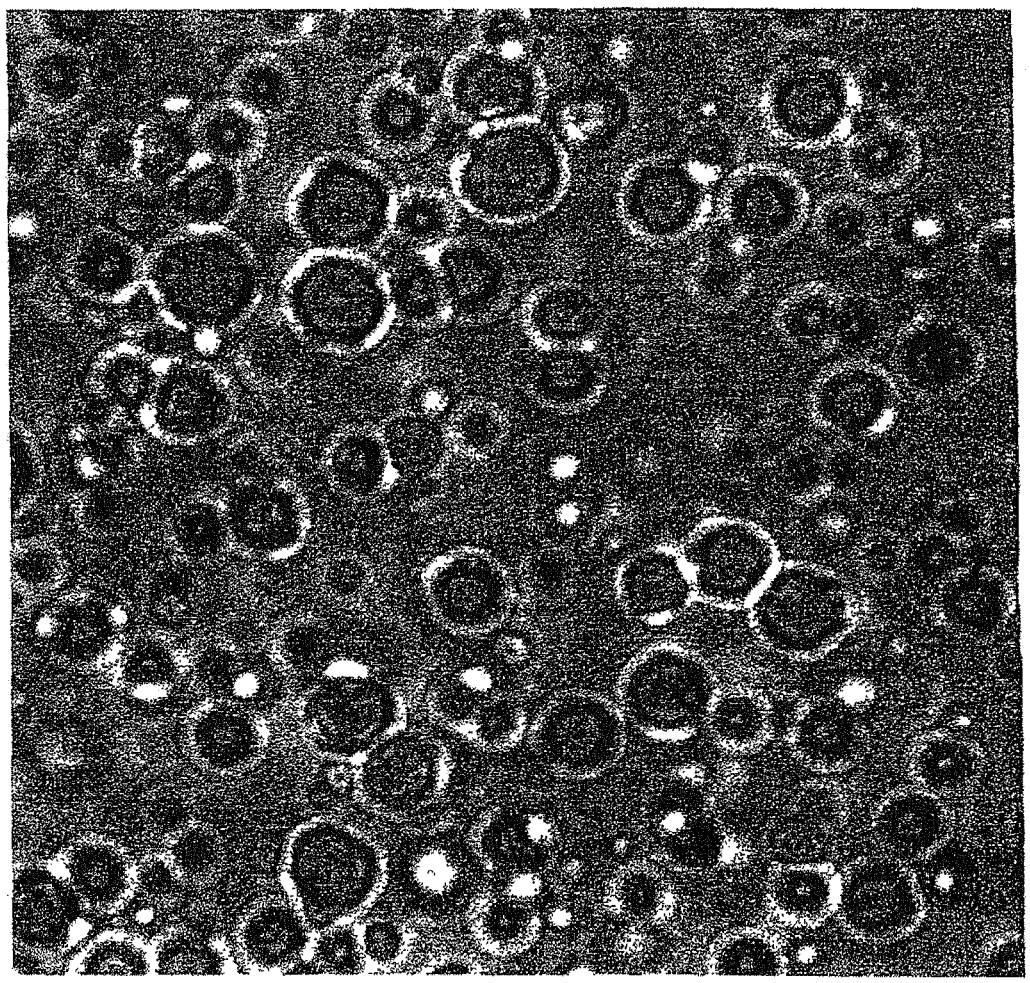
FIGS. 4a and 4b are light micrographs of benzoyl peroxide encapsulated in the microcapsules of the present invention, prior to its release (FIG. 4a) and after its release by a rubbing action (FIG. 4b) according to the present invention.
Figure 4B:
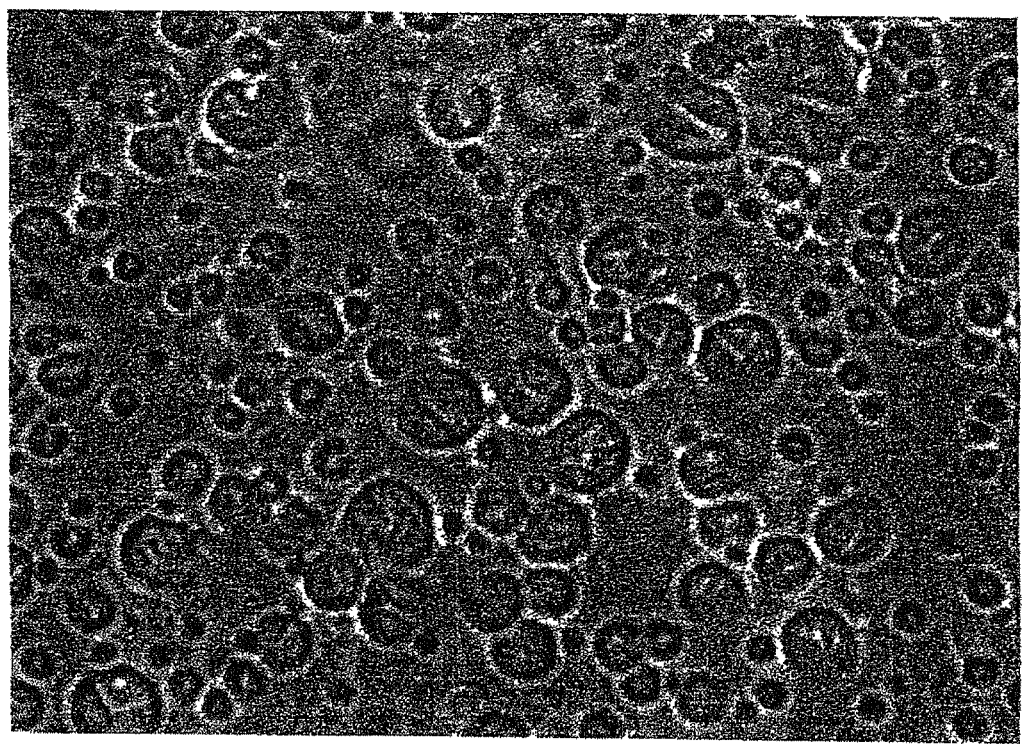

A drop of a diluted sample (1:10 suspension to water) of the silica dispersion prepared as described under Example 6, containing 4% (w/w) encapsulated benzoyl peroxide, was poured between two glass slides. Light microscopic examination of the sample revealed intact particles in the suspension with a mean particle size of roughly 10μ (FIG. 4*a*). The release of the active ingredient, BPO, from the silica dispersion was accomplished via gentle pressure exerted on the top glass microscope slide with a finger. Re-examination of the slide revealed the presence of broken and distorted microspheres (FIG. 4*b*). Further pressure results in the complete rupture of the silica shell, liberating all entrapped oil phase contents.

Example 10

Release of BPO from Microcapsules by Capsule Drying

Figure 5A:
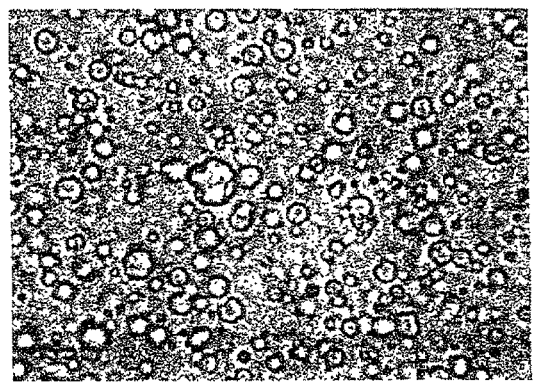
FIGS. 5a and 5b are light micrographs of benzoyl peroxide is encapsulated in the microcapsules of the present invention, prior to its release (FIG. 5a) and after its release by heating (FIG. 5b) according to the present invention.
Figure 5B:
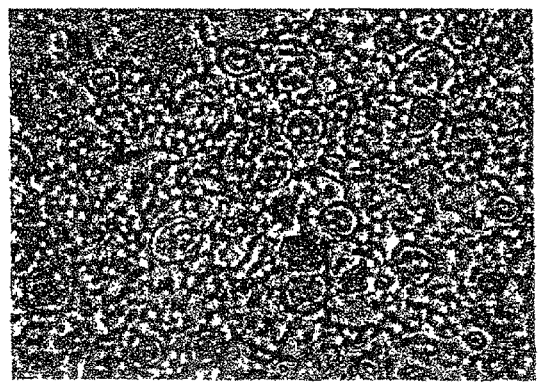

A drop of a silica dispersion prepared as described under Example 6 was poured onto a glass slide. After light microscopic examination (FIG. 5*a*), the sample was heated to 40° C., for 24 hours. Re-examination of the slide revealed the presence of broken and distorted microspheres (FIG. 5*b*).

Examples 1-10 demonstrate that unstable active ingredients can be encapsulated in microcapsules, and a composition for topical application can be formed, according to the present invention. The active ingredient can be encapsulated alone or can be co-encapsulated with a stabilizing material, as in Example 2. The composition can be designed so that the microcapsules will release their contents after topical application, by using, for example, a high water content within the carrier surrounding the microcapsules (as in Example 8), a rubbing action (as in Example 9), a drying procedure (as in Example 10) or any other release mechanism.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A therapeutic or cosmetic composition for topical application comprising a plurality of microcapsules each having a core-shell structure,
   wherein said core is encapsulated within said shell and includes at least one active ingredient, said core being in the form selected from the group consisting of an emulsion, an oil solution, and a dispersion,
   wherein the shell consists essentially of at least one metal oxide inorganic polymer obtained by a sol-gel process using a sol-gel precursor, said sol-gel precursor being (i) a monomer, (ii) a partially hydrolyzed and partially condensed polymer of said monomer, or mixtures of (i) and (ii), said monomer (a) being selected from the group consisting of a metal alkoxide monomer, a semi-metal alkoxide monomer, a metal ester monomer, a semi-metal ester monomer, and a silazane monomer, or (b) having a formula $M(R)_n$, wherein M is a metallic or a semi-metallic element, R is a hydrolysable substituent, and n is an integer from 2 to 6, and
   wherein said composition stabilizes said at least one active ingredient prior to topical application and releases said at least one active ingredient from said microcapsules following topical application.

2. The composition of claim 1, further comprising a pharmaceutically, cosmetically or cosmeceutically acceptable carrier.

3. The composition of claim 2, wherein said acceptable carrier comprises at least one auxiliary agent, and wherein said auxiliary agent triggers the release of said at least one active ingredient from said microcapsules upon said topical application.

4. In a method for treating a skin condition in a subject in need thereof, comprising topically applying onto the skin a composition containing a substance suitable for the treatment of the skin condition, the improvement wherein said composition is a composition in accordance with claim 1 in which said active ingredient is the substance suitable for the treatment of the skin condition.

5. A method of delivering an active ingredient for topical application, comprising:
   formulating the active ingredient into a therapeutic or cosmetic composition in accordance with claim 1;
   topically applying the therapeutic or cosmetic composition; and
   causing said microcapsules to disintegrate.

6. A method for delivering an active ingredient from a therapeutic or cosmetic composition in accordance with claim 1, comprising:
   topically applying said therapeutic or cosmetic composition; and
   causing said microcapsules to disintegrate.

7. In a method of treating a skin, hair, ear, mucosal membrane, rectal, nasal or dental condition in a subject in need thereof comprising topically applying onto a skin, hair, ear, mucosal membrane, rectum, nose or tooth, an active ingredient capable of treating the skin, hair, ear, mucosal membrane, rectal, nasal or dental condition, the improvement wherein said active ingredient is formulated within a therapeutic or cosmetic composition in accordance with claim 1.

8. A therapeutic or cosmetic composition for topical application comprising a plurality of microcapsules each having a core-shell structure,
   wherein said core is encapsulated within said shell and includes at least one active ingredient, said core being in the form selected from the group consisting of an emulsion, an oil solution, and a dispersion,
   wherein the shell consists essentially of at least one metal oxide inorganic polymer obtained by a sol-gel process using a sol-gel precursor, said sol-gel precursor being (i) a monomer, (ii) a partially hydrolyzed and partially condensed polymer of said monomer, or mixtures of (i) and (ii), said monomer (a) being selected from the group consisting of a metal alkoxide monomer, a semi-metal alkoxide monomer, a metal ester monomer, a semi-metal ester monomer, and a silazane monomer, or (b) having a formula $M(R)_n$, wherein M is a metallic or a semi-metallic element, R is a hydrolysable substituent, and n is an integer from 2 to 6, and
   wherein said composition stabilizes said at least one active ingredient prior to topical application and releases said at least one active ingredient from said microcapsules following topical application, said release of said at least one active ingredient from said microcapsules being the result of an action selected from the group consisting of rubbing or spreading action, drying, contacting said microcapsules with an auxiliary agent, extraction of an active ingredient, and any combination thereof.

9. A therapeutic or cosmetic composition for topical application comprising a pharmaceutically, cosmetically or cosmeceutically acceptable carrier and a plurality of microcapsules each having a core-shell structure,
   wherein said core is encapsulated within said shell and includes at least one active ingredient, said core being in the form selected from the group consisting of an emulsion, an oil solution, and a dispersion,
   wherein the shell consists essentially of at least one metal oxide inorganic polymer obtained by a sol-gel process using a sol-gel precursor, said sol-gel precursor being (i) a monomer, (ii) a partially hydrolyzed and partially condensed polymer of said monomer, or mixtures of (i) and (ii), said monomer (a) being selected from the group consisting of a metal alkoxide monomer, a semi-metal alkoxide monomer, a metal ester monomer, a semi-metal ester monomer, and a silazane monomer, or (b) having a formula $M(R)_n$, wherein M is a metallic or a semi-metallic element, R is a hydrolysable substituent, and n is an integer from 2 to 6,
   wherein said pharmaceutically, cosmetically or cosmeceutically acceptable carrier comprises at least one auxiliary agent, and wherein said auxiliary agent triggers the release of said at least one active ingredient from said microcapsules upon said topical application, and wherein said composition stabilizes said at least one active ingredient prior to topical application and releases said at least one active ingredient from said microcapsules following topical application.

10. The composition of claim 9, comprising at least two microcapsules each of said at least two microcapsules containing a different active ingredient.

11. The composition of claim 9, wherein the at least one active ingredient is benzoyl peroxide and the composition further comprises one or more microcapsules, each containing one or more active ingredient(s) other than benzoyl peroxide.

12. The composition of claim 9, wherein said at least one active ingredient is selected from the group consisting of a vitamin and an anti-acne agent.

13. The composition of claim 12, wherein said vitamin is a retinoid.

14. The composition of claim 12, wherein said anti-acne agent is benzoyl peroxide.

* * * * *